US008702766B2

(12) United States Patent
Mueller

(10) Patent No.: US 8,702,766 B2
(45) Date of Patent: Apr. 22, 2014

(54) LOCKING DEVICE FOR FIXATION MECHANISM OF MEDICAL IMPLANT

(75) Inventor: Michael M. Mueller, Union, MO (US)

(73) Assignee: CoreLink, LLC, Fenton, MI (US)

( * ) Notice: Subject to any disclaimer, the term of this patent is extended or adjusted under 35 U.S.C. 154(b) by 110 days.

(21) Appl. No.: 13/530,265

(22) Filed: Jun. 22, 2012

(65) Prior Publication Data
US 2013/0006314 A1 Jan. 3, 2013

Related U.S. Application Data

(60) Provisional application No. 61/501,981, filed on Jun. 28, 2011.

(51) Int. Cl.
A61B 17/80 (2006.01)
(52) U.S. Cl.
USPC ............................. 606/295; 606/292; 606/289
(58) Field of Classification Search
USPC .......................................... 606/289, 292–295
See application file for complete search history.

(56) References Cited

U.S. PATENT DOCUMENTS 8,454,667 B2 * 6/2013 Humphreys .................. 606/289

* cited by examiner

Primary Examiner — Andrew Yang
(74) Attorney, Agent, or Firm — Thompson Coburn LLP

(57) ABSTRACT

A receiving member has a primary socket for a fixation mechanism and a secondary socket for a locking device. The secondary socket has a first bore intersecting a portion of the primary socket and forming an arcuate cut-out. The secondary socket has a chord member extending into the secondary socket first bore that forms a radial undercut in the secondary socket. The secondary socket has a detent extending from the radial undercut into the chord member. The locking device is rotatable in the secondary socket between an unlocked position in which an engagement surface of a cap of the locking device is angularly displaced from the arcuate cut-out, and a locked position in which the cap engagement surface occupies the arcuate cut-out and engages the fixation mechanism, and the arm engages an underside of the chord member, thereby preventing the fixation member from disengaging the receiving member primary socket.

21 Claims, 28 Drawing Sheets

LOCKING DEVICE FOR FIXATION MECHANISM OF MEDICAL IMPLANT

RELATED APPLICATION DATA

The application claims priority to provisional application Ser. No. 61/501,981 filed Jun. 28, 2011, the disclosure of which is incorporated by reference herein.

BACKGROUND

The disclosure relates to a device for locking a bone fastening or fixation mechanism in a receiving member of a medical implant. The bone fastening or fixation mechanism is used to mount the receiving member to a bone structure in the medical implant. The locking device prevents the bone fastening mechanism from backing out of the receiving member.

DETAILED DESCRIPTION

Figure 1:
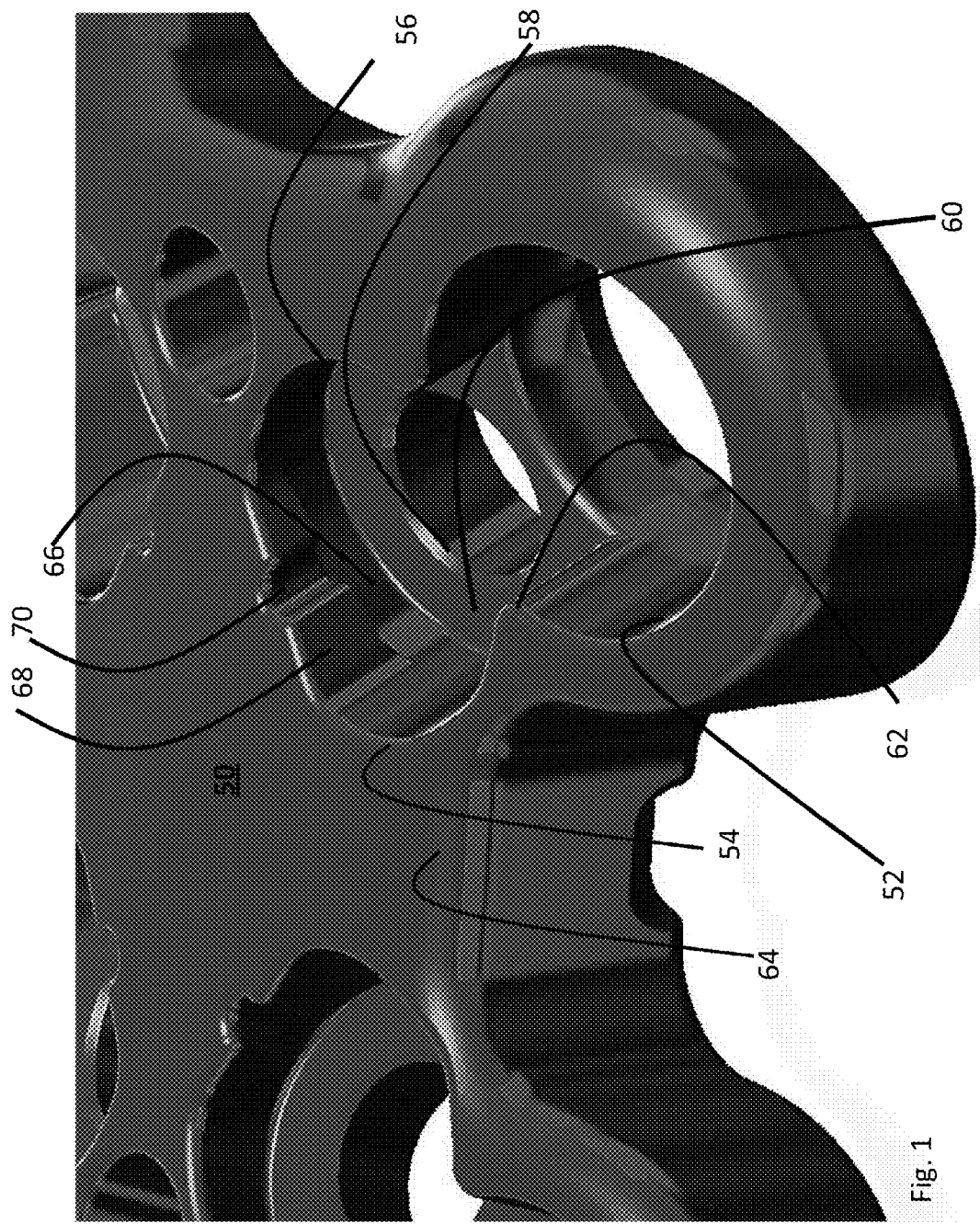
FIG. 1 is perspective view of a receiving member comprising an anterior lumbar plate.

The locking device is intended to be used in connection with a fixation mechanism, for instance, a screw, used in a receiving member 50 of a surgical implant. In one example, for instance, as shown in the drawings herein, the receiving member 50 comprises an anterior lumbar plate and the locking device may be used in the anterior lumbar plate to prevent the fixation screws that mount the lumber plate to the bone structure from "backing out" of or away from the lumbar plate. In an alternate embodiment, the locking device may be used in a receiving member comprising an anterior cervical plate to prevent the fixation screws that mount the cervical plate to the bone structure from "backing out" from the cervical plate and the bone structure. It is contemplated that the locking device may be used in connection with other fixation mechanisms, for instance, fixation screws, and receiving members in other applications to prevent the fixation mechanism from backing out of the receiving member and the bony structure. Accordingly, the receiving members may include other bone implant devices or other surgically implanted devices where fixation mechanisms are attached to bones. For the purposes of simplifying the discussion herein, the description will make reference to a receiving member comprising an anterior lumbar plate and a locking device used in connection therewith. It should be appreciated that other receiving members may incorporate the principles described herein. Thus, the description that follows below is not necessarily limited to receiving members comprising anterior lumbar plates but other surgical implants.

FIG. 1 shows a receiving member 50 comprising an anterior lumbar plate. The receiving member 50 has a primary socket 52 into which a fixation mechanism, for instance, a bone screw, is located. The primary socket 52 has a contour that enables the fixation mechanism to articulate in the primary socket. Accordingly, the primary socket may be spherically shaped to provide articulation. The underside of the cap of the fixation mechanism (i.e., the cap of the screw) may have a matching contour thus promoting articulation of the screw relative to the socket. In that regard, the primary socket may be a countersunk hole or a tapered bore. The primary socket may also have other configurations depending upon the application and the geometry associated with the fixation mechanism, for instance, the underside surface of the cap of the fixation mechanism.

Figure 2:
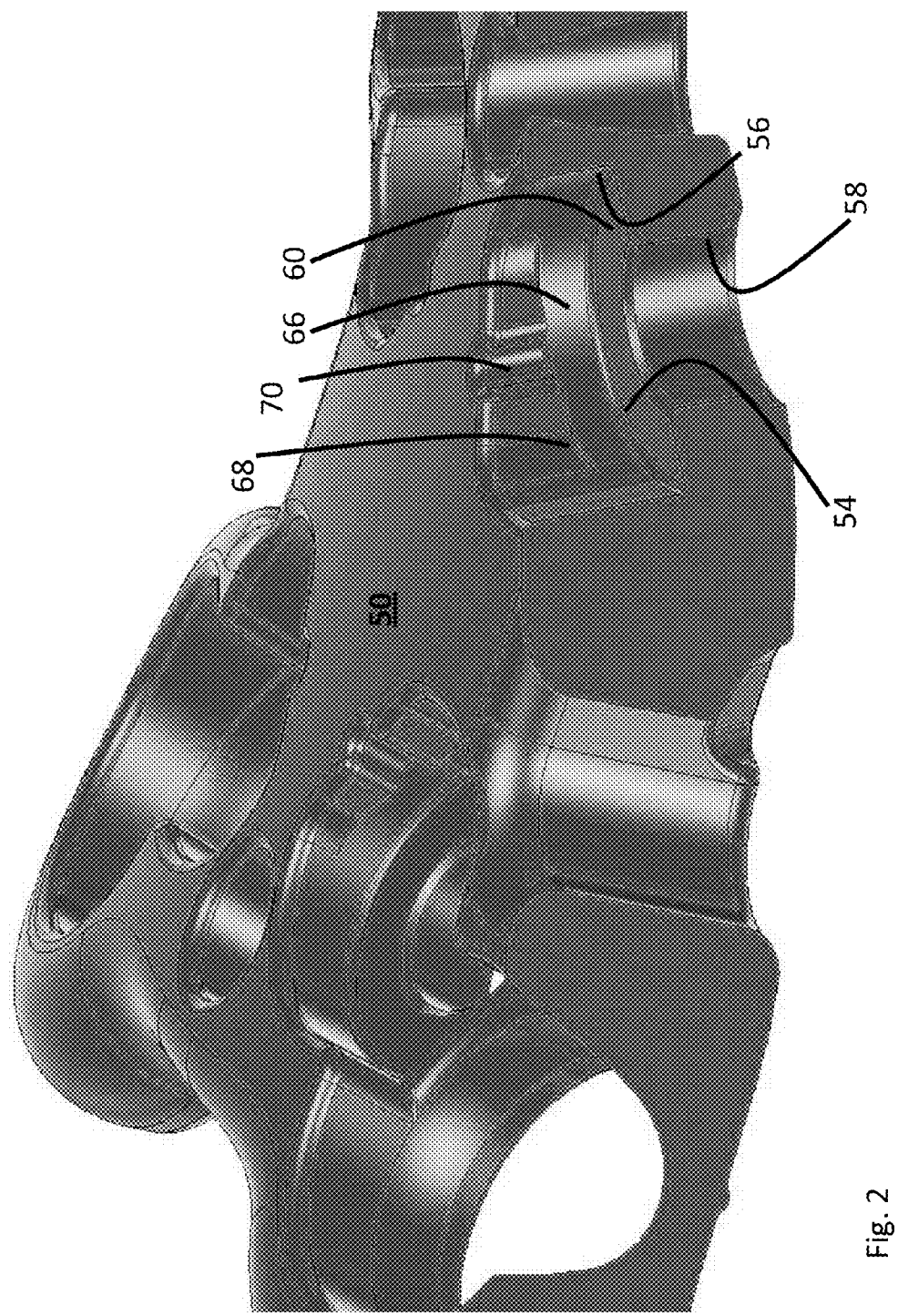
FIG. 2 is a perspective cross sectional view of the anterior lumbar plate of FIG. 1.
Figure 3:
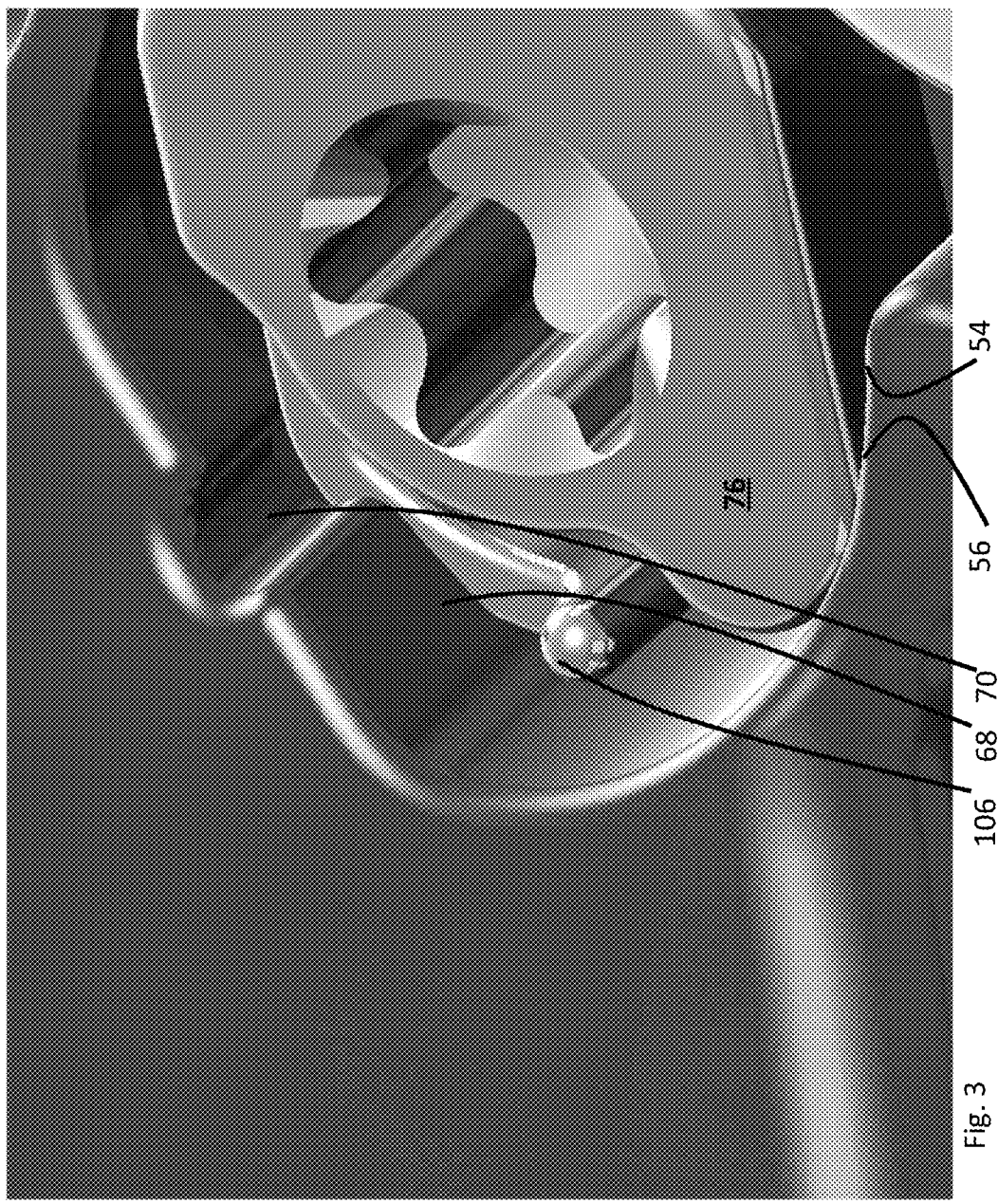
FIG. 3 is an enlarged perspective view of the anterior lumbar plate of FIG. 1 with a locking device installed.

Adjacent to the primary socket 52 is a secondary socket 54. The secondary socket has first and second bores 56, 58 with the first bore generally greater in diameter than the second bore thereby forming a counter bored shoulder 60 in the secondary socket. The first bore 56 has a diameter dimensioned such that the first bore intersects with the primary socket 52 and creates an arcuate cutout 62 between the primary and secondary sockets. As shown in the drawings, the primary and secondary sockets 52, 54 form a single recess in the receiving member 50 through the arcuate cut-out 62. As best shown in FIGS. 2 and 3, the first bore 56 of the secondary socket is not entirely cylindrical from a top surface 64 of the receiving member to the counter bored shoulder 60. The first bore 56 includes a radial undercut 66 opposite the arcuate cut-out 62. The radial under cut 66 extends between the counter bore shoulder 60 and an intermediate portion of first bore 56 thus forming a chord member 68 axially above the radial under cut. A radial detent 70 extends through the chord member 68 into the radial under cut 66. The radial under cut 66 and corresponding chord member 68 of the secondary socket is preferably arranged 180 degrees from the arcuate cutout 62 of the secondary socket. Other arrangements may also be used so that the cap of one locking device may be used to engage the cap of several fixation mechanisms provided in adjacent primary sockets intersecting with one secondary socket. The secondary socket second bore 58 extends through a bottom surface 72 of the receiving member 50.

Figure 4:
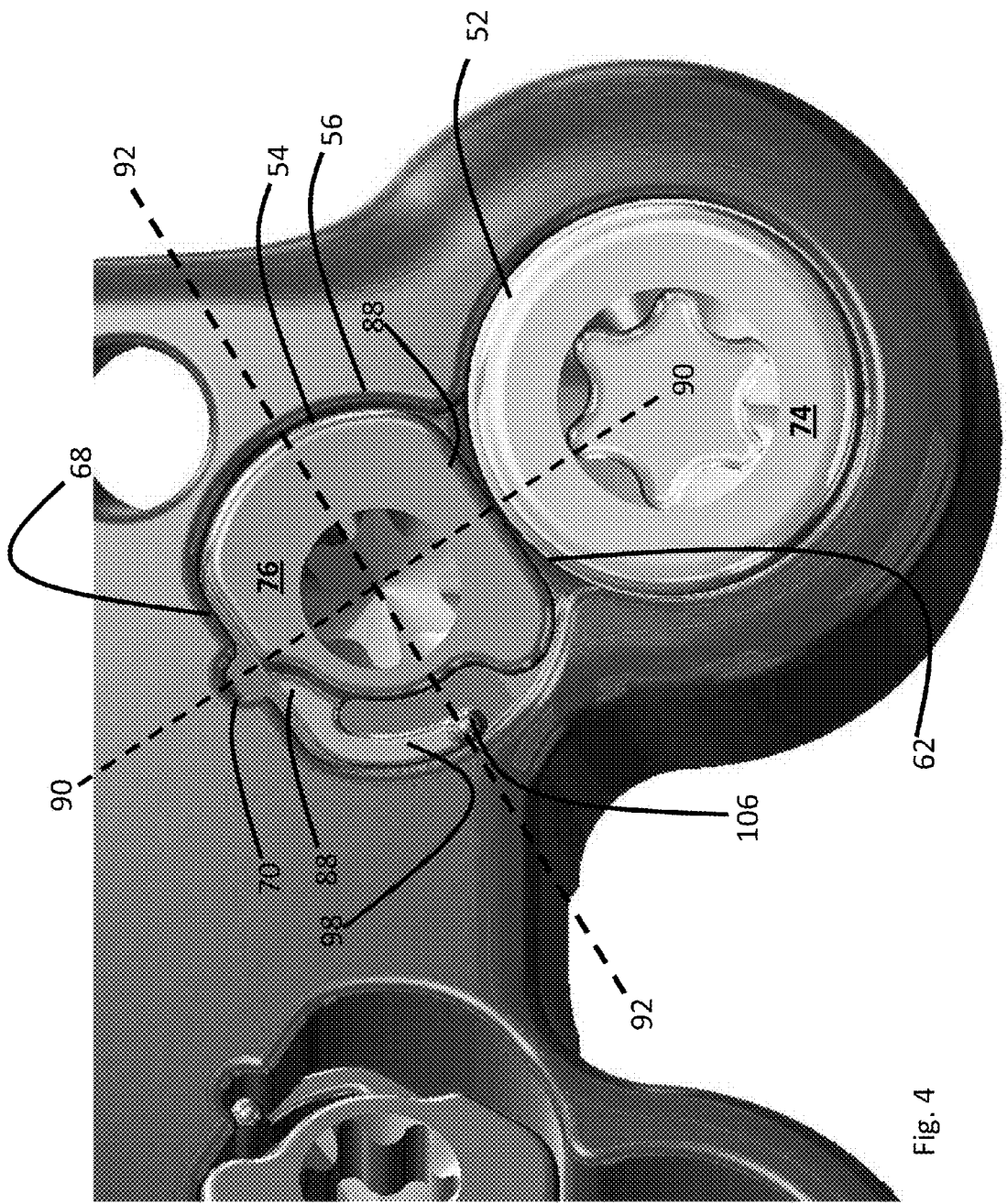
FIG. 4 is a top view of a portion of the anterior lumbar plate of FIG. 1 showing a bone fastening mechanism and a locking device for the bone fastening mechanism in an unlocked position.
Figure 5:
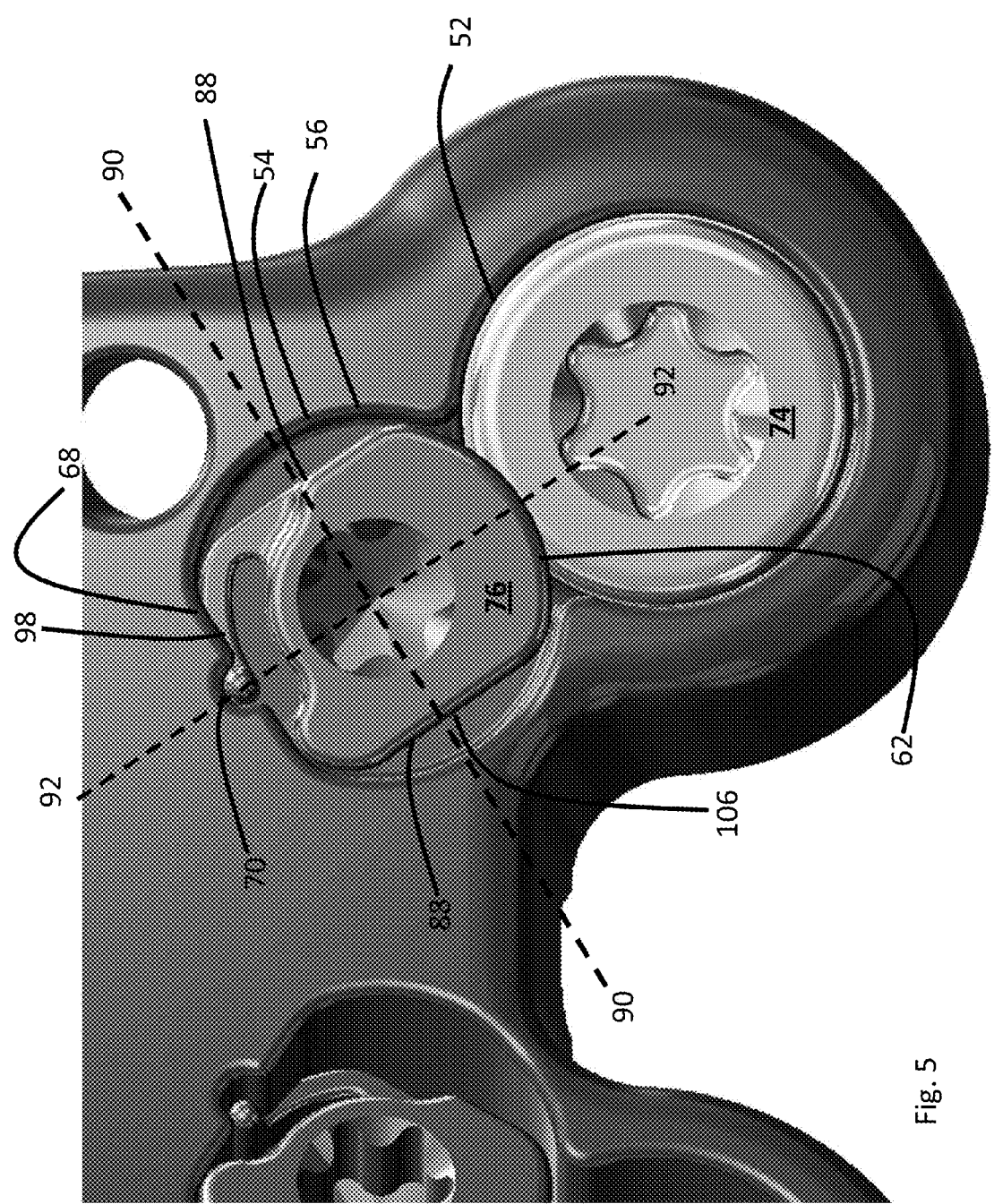
FIG. 5 is a top view of a portion of the anterior lumbar plate of FIG. 1 showing a bone fastening mechanism and a locking device for the bone fastening mechanism in a locked position.
Figure 6:
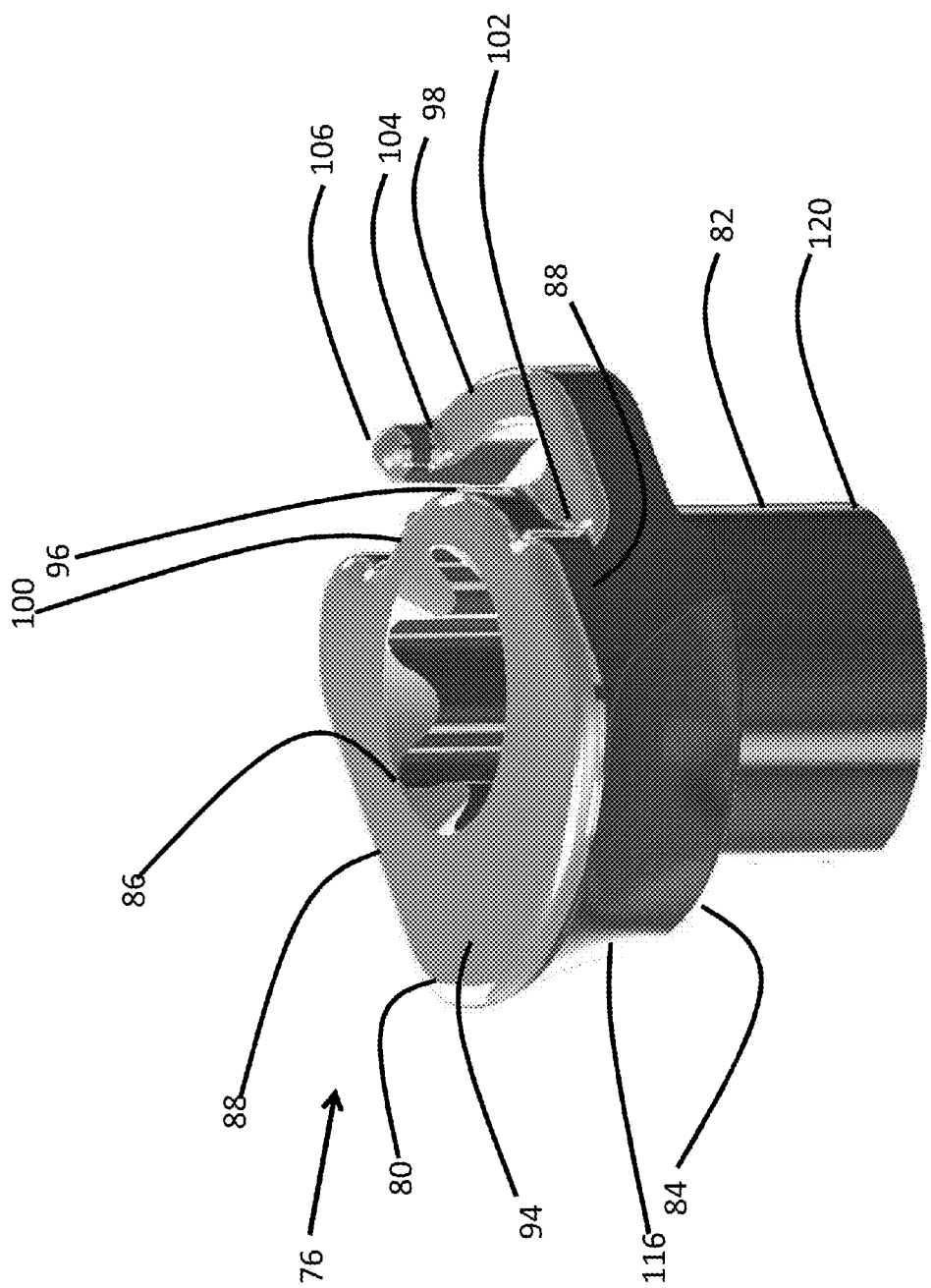
FIG. 6 is a top perspective view of the locking device shown in FIGS. 4 and 5.
Figure 7:
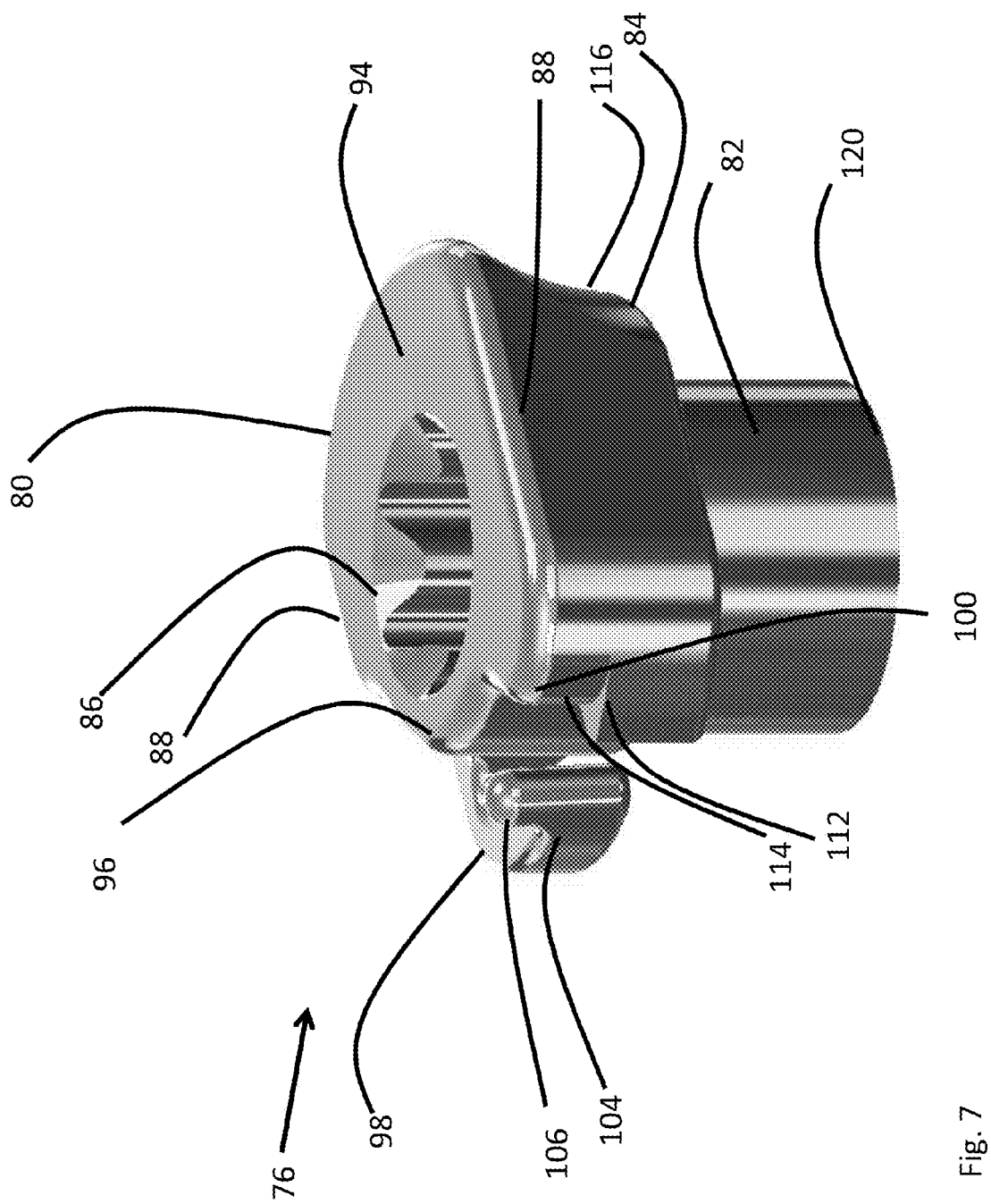
FIG. 7 is an alternate top perspective view of the locking device of FIGS. 4 and 5.
Figure 8:
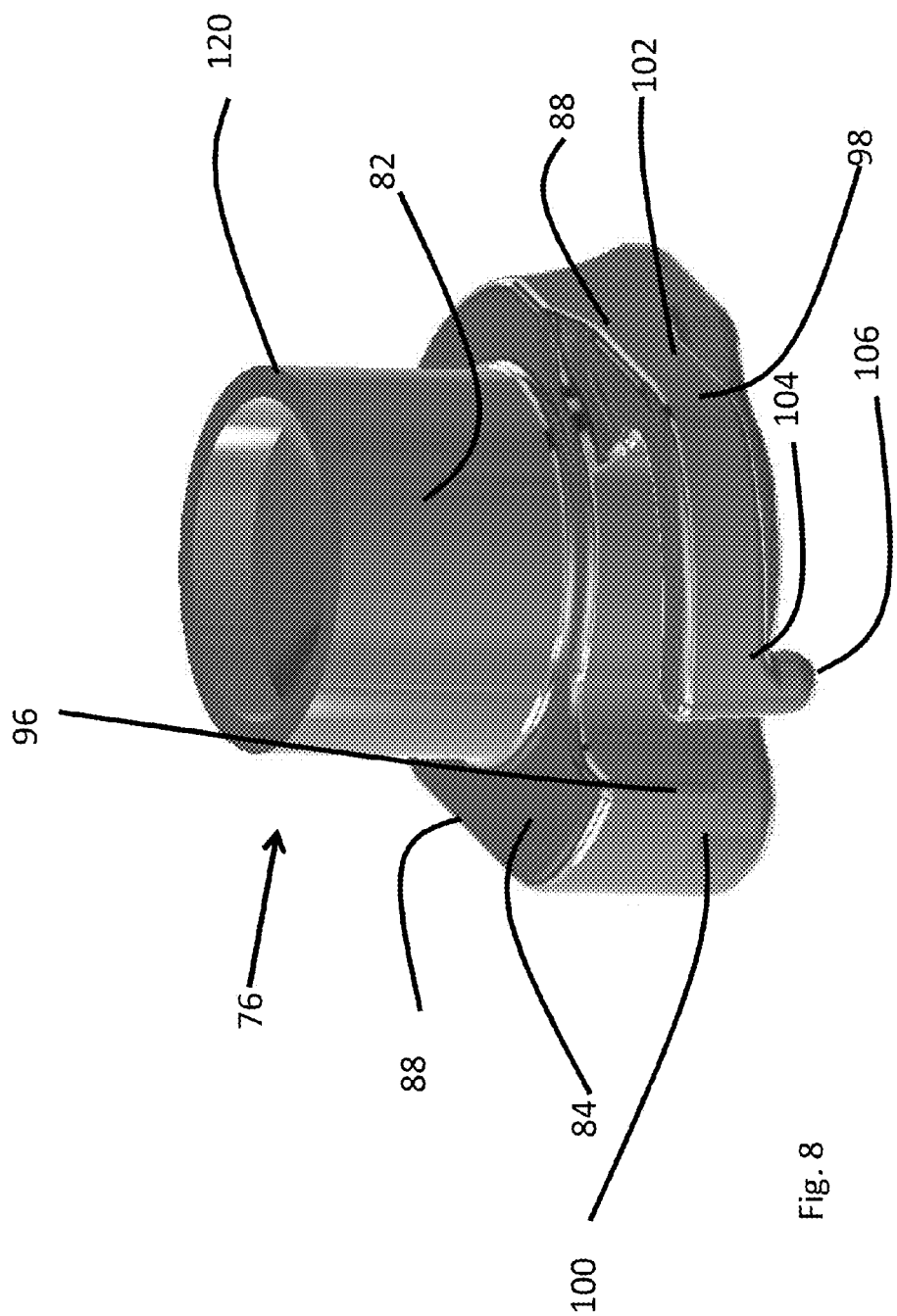
FIG. 8 is a bottom perspective view of the locking device of FIGS. 4 and 5.
Figure 9:
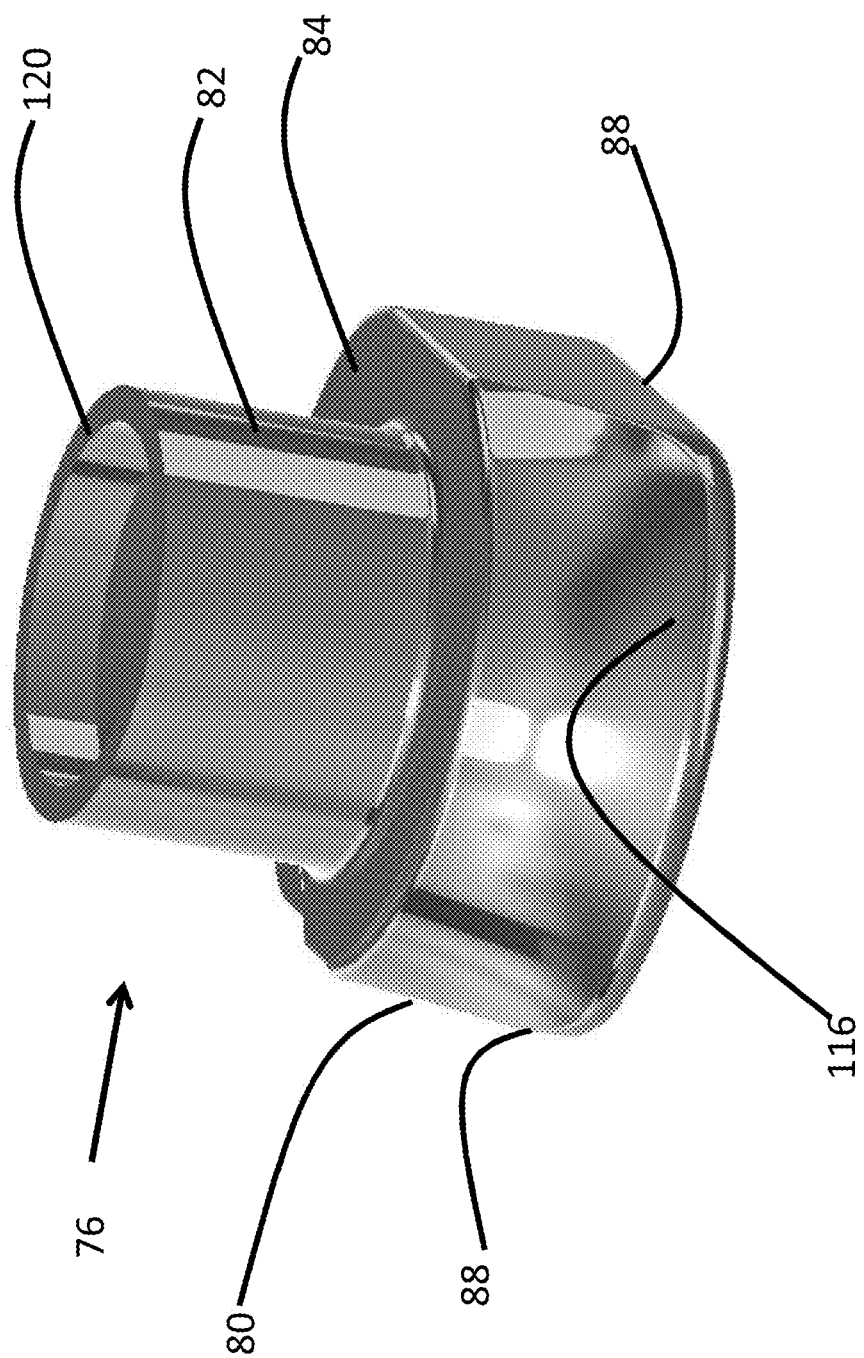
FIG. 9 is an alternate bottom perspective view of the locking device of FIGS. 4 and 5.
Figure 10:
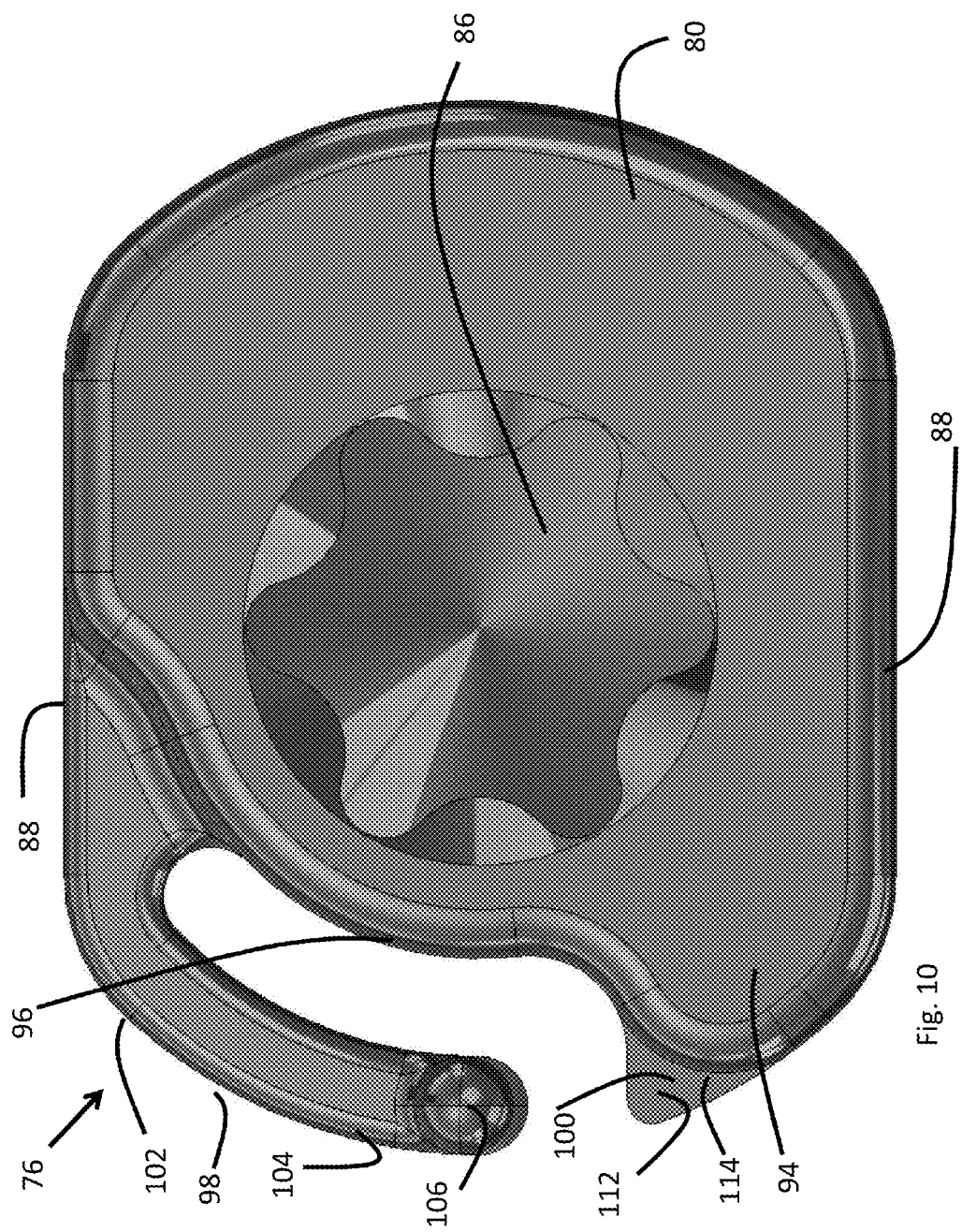
FIG. 10 is a top view of the locking device of FIGS. 4 and 5.
Figure 11:
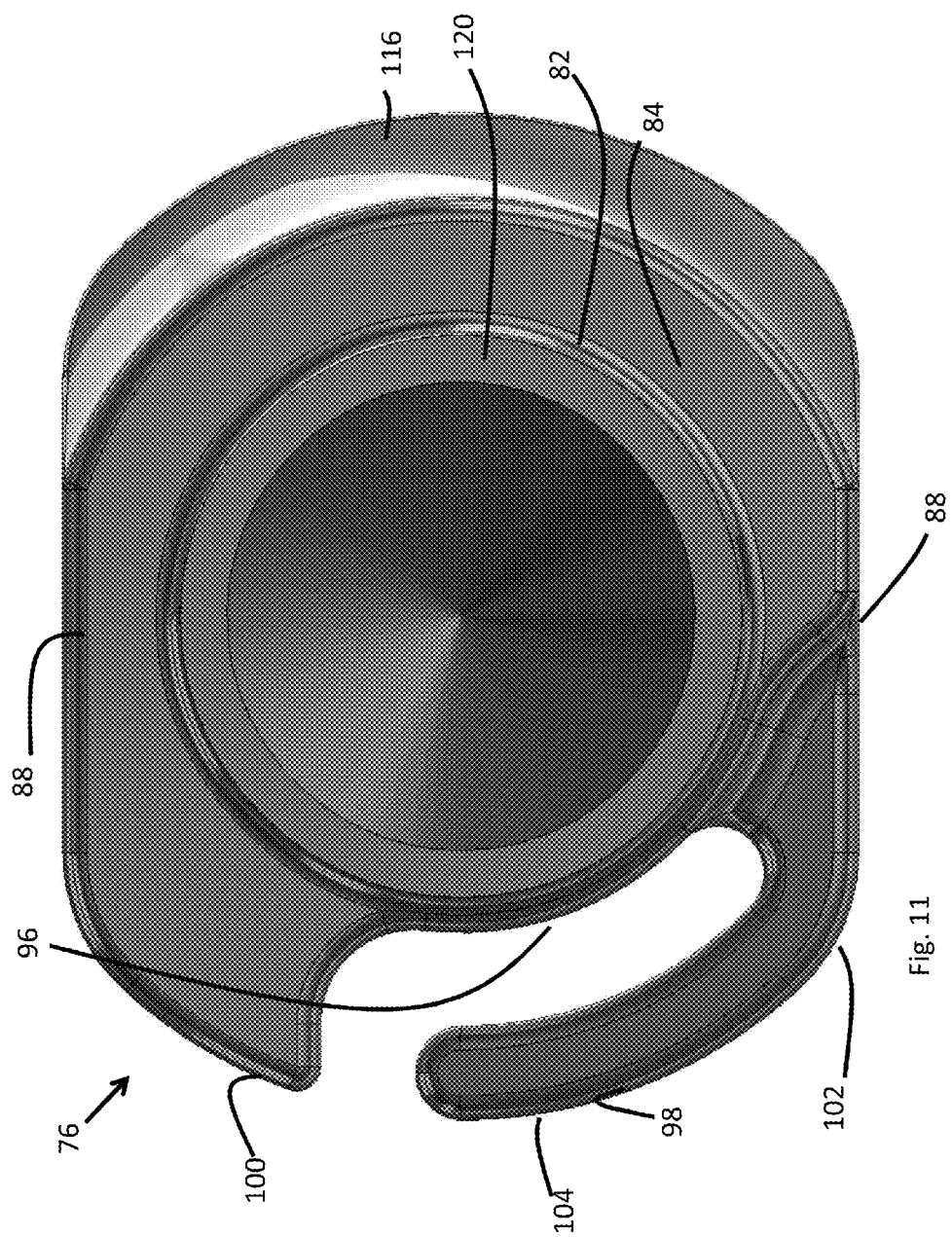
FIG. 11 is a bottom view of the locking device of FIGS. 4 and 5.
Figure 12:
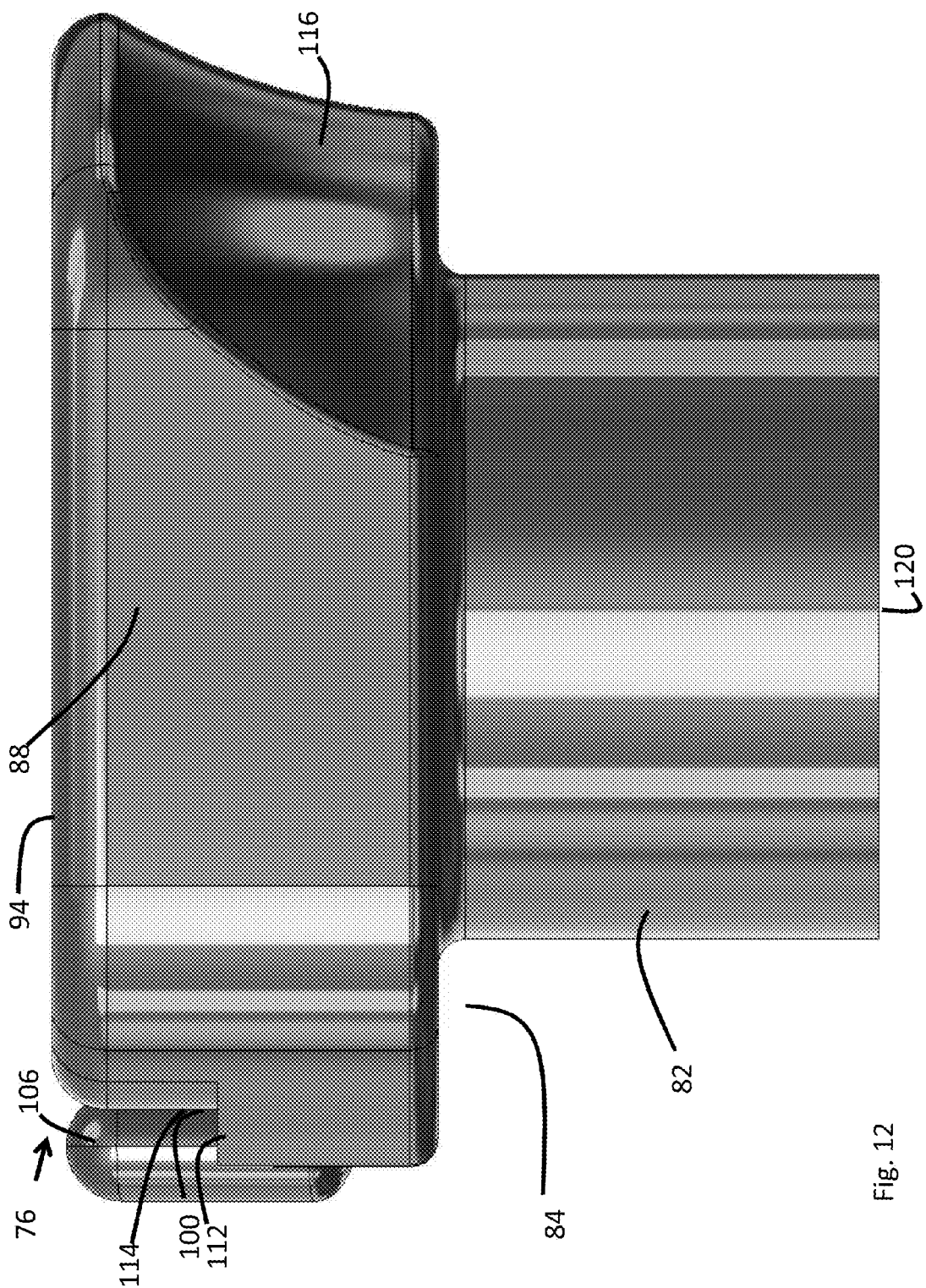
FIG. 12 is a front view of the locking device of FIGS. 4 and 5.
Figure 13:
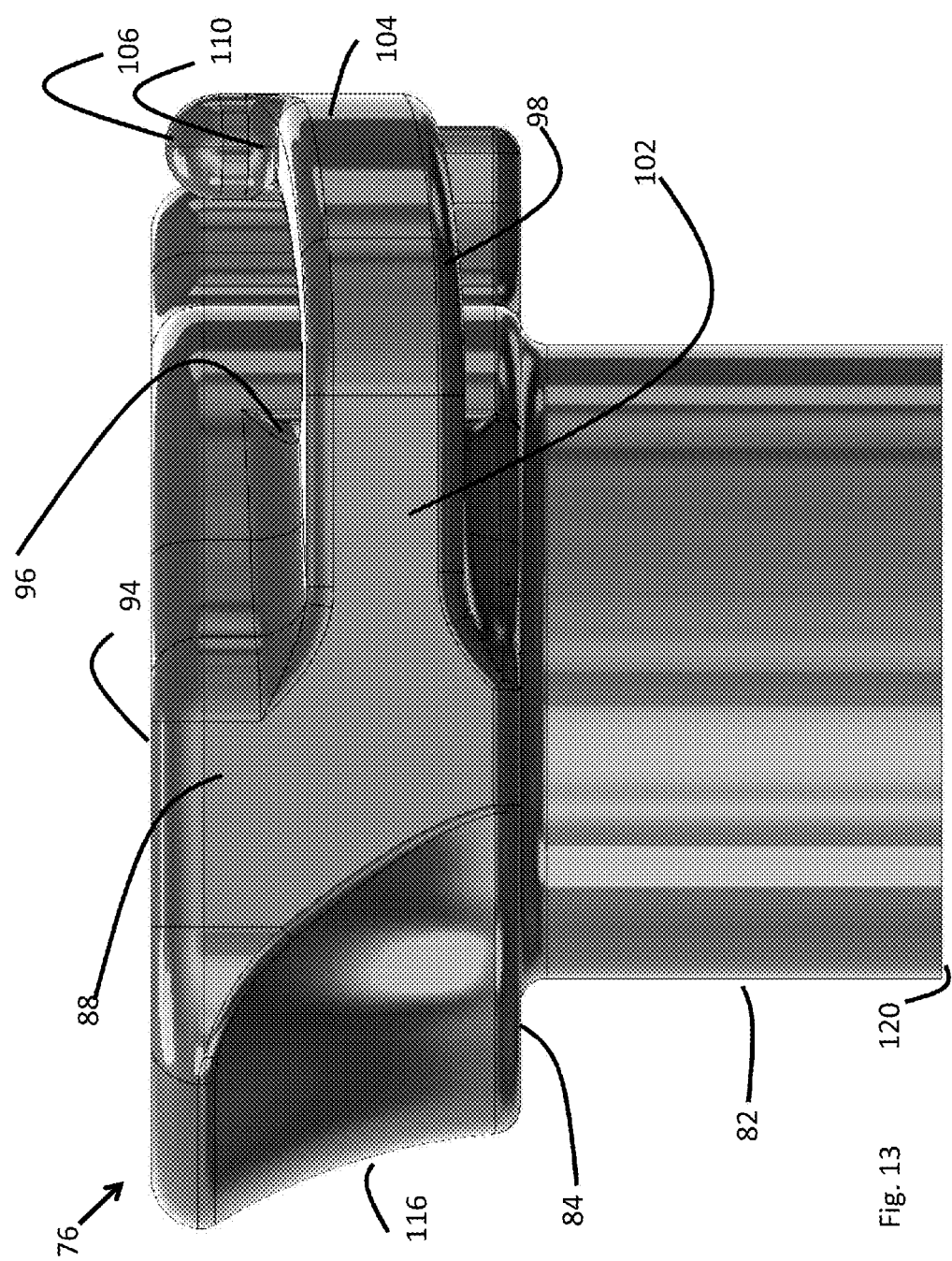
FIG. 13 is a rear view of the locking device of FIGS. 4 and 5.

As shown in FIGS. 3, 4 and 5, the primary socket 52 is adapted to receive a fixation mechanism 74, and the secondary socket 54 is adapted to receive a locking device 76 as described in further detail below. The fixation mechanism 74 is inserted through the primary socket 52 such that a portion of a cap 78 of the fixation mechanism 74 partially extends into the secondary socket 54 through the arcuate cutout 62. FIG. 4 provides a view where the locking device 76 is positioned in a first position or unlocked position and does not obstruct the arcuate cutout 62 thereby allowing the fixation mechanism 74 to be inserted in the primary socket 52 without interference between the locking device and the cap 78 of the fixation mechanism. FIG. 5 provides an alternate view where the locking device 76 is rotated (in FIG. 5-*clockwise* 90 degrees) to a second position in which a portion of the locking device extends through the arcuate cutout 62 to a position over the cap 78 of the fixation mechanism 74. In the second or locked position, the locking device 76 prevents the fixation mechanism 74 from backing out of or away from the primary socket 52. As will be described in further detail, the locking device 76 is adapted to cooperate with the cap 78 of the fixation mechanism to allow articulation of the fixation mechanism in the primary socket of the receiving member when the locking device is in the second or locked position. And, as described below in greater detail, the locking device 76 is configured to also prevent the fixation mechanism from backing out of the primary socket and any bone structure to which the fixation mechanism is mounted.

The locking device, the fixation mechanism and/or the receiving member may be made from a medical grade titanium, for instance, Ti-6Al-4V.

Further detail of one embodiment of the locking device 76 (i.e., the locking device of FIGS. 4 and 5) is shown in FIGS. 6-15. The locking device 76 comprises a cap 80 portion with a stem 82 extending axially through a center of the cap portion. The stem is preferably a cylindrical member having a diameter that matches the diameter of the second bore 58 of the secondary socket 54. The flat counter bored shoulder 60 formed between the first and second bores 56,58 in the secondary socket provides a bearing surface on which an underside surface 84 of the cap of the locking device rides as it rotates between first and second positions.

The cap portion 80 has an actuation center 86 enabling a user to rotate the locking device between first and second positions (i.e., between the positions shown in FIGS. 4 and 5) with an operator tool. The actuation center 86 may have a hexalobe drive feature in accordance with ISO 10664. Other drive features may also be used as desired.

The cap portion 80 has a generally circular outer periphery with chord portions 88 extending across the outer periphery thereby providing the cap portion with a minor diameter 90 as measured between diametrically opposite chord portions, and a major diameter 92 as measured between diametrically opposite cylindrical surfaces on the outer periphery of the cap. The cap major diameter 92 matches the diameter of the secondary socket first bore 56 as measured in the radial undercut 66 of the first bore.

Figure 23:
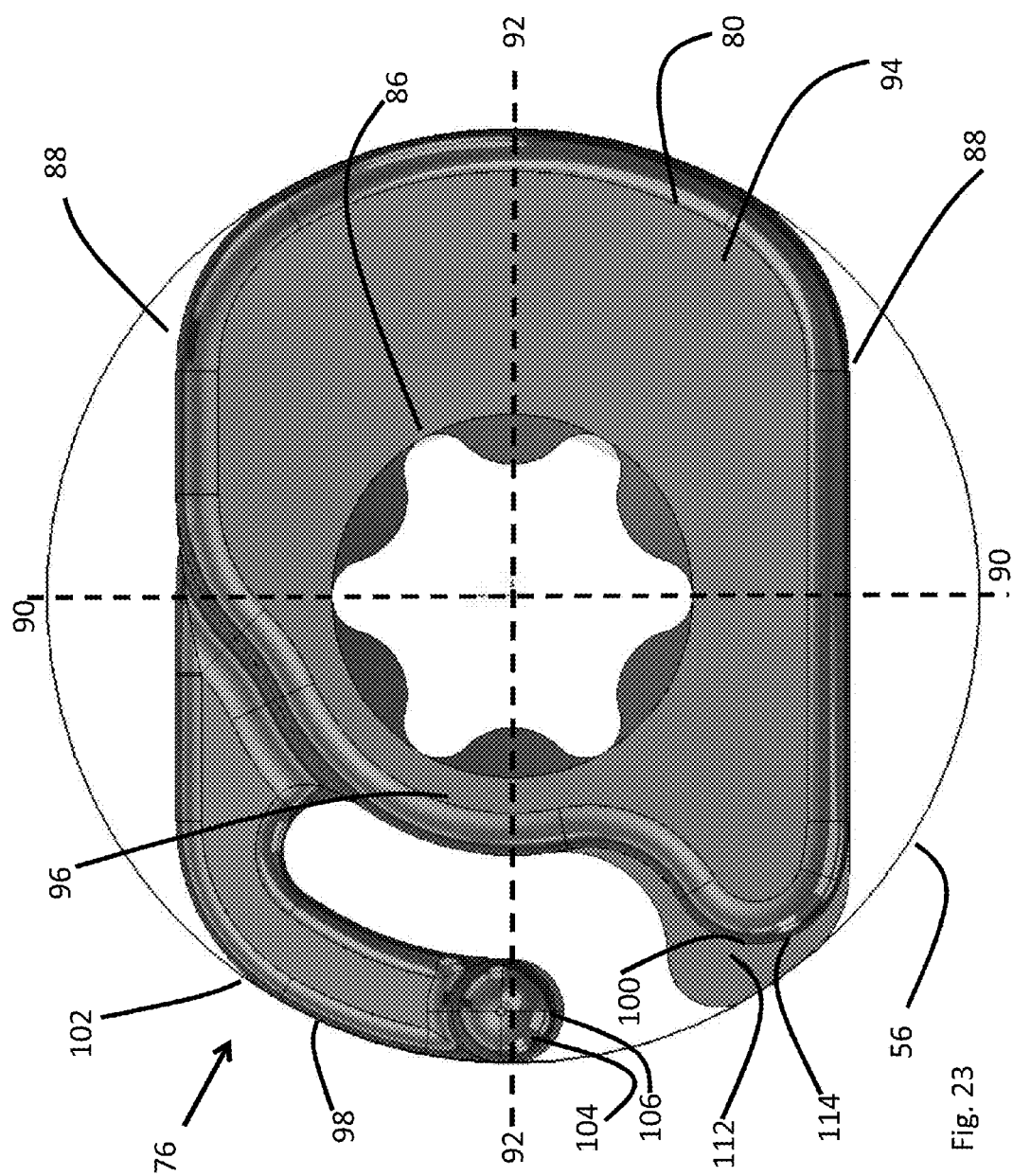
FIG. 23 is a top view showing a circular configuration of an outer periphery of a cap of the locking device of FIG. 16.
Figure 24:
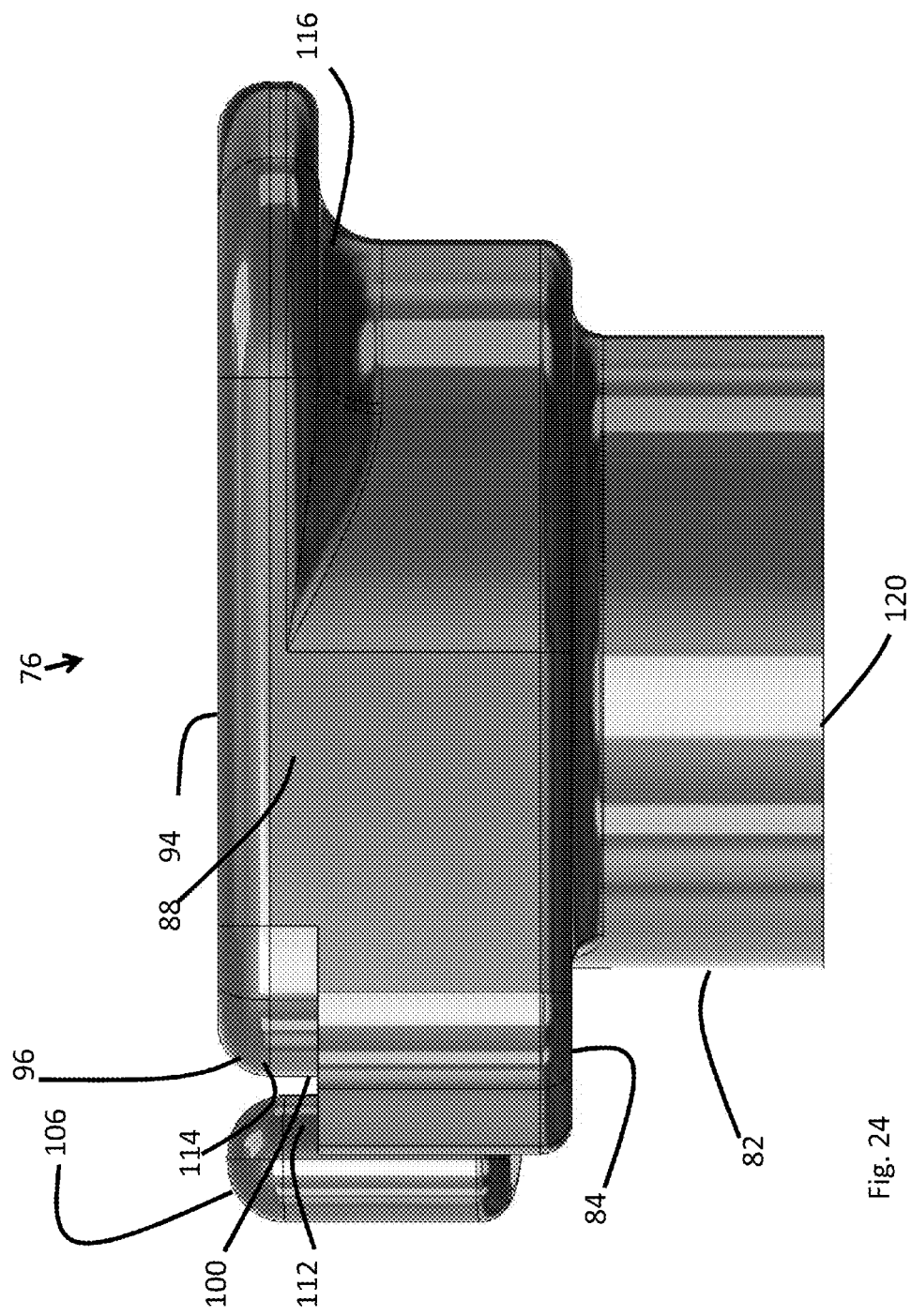
FIG. 24 is a front view of the locking device of FIG. 16.

A top surface 94 of the cap has an external relief area 96 generally aligned with the major diameter 92 to provide clearance under the chord member 68 of the secondary socket extending above the radial undercut 66 of the first bore. The external relief area 96 on the top surface 94 of the cap of the locking device allows the locking device to be rotated between the first and second positions. The external relief area 96 of the cap portion includes a resiliently deflectable arm 98 and a positive stop 100, which cooperate with the chord member 68 of secondary socket first bore to releasably lock the locking device in the second position as shown in FIG. 5. The resiliently deflectable arm 98 extends from the cap portion in the external relief area 96 and defines at least a portion of the major diameter 92. Diametrically opposite the resilient arm, the cap has outer periphery with a cylindrical surface close to the top surface 94 of the cap. This is further illustrated in FIG. 23, which shows a locking device positioned in the first bore within the radial cut-out, thereby allowing the locking device to rotate in the secondary socket first bore in the radial cut-out. The minor diameter 90 is sized such that minor diameter portion of the cap of the locking device does not extend through the arcuate cut-out 62, and to allow the fixation mechanism to be inserted in the primary socket without interference from the minor diameter portion of the cap of the locking device. (See, FIGS. 4 and 5).

Figure 14:
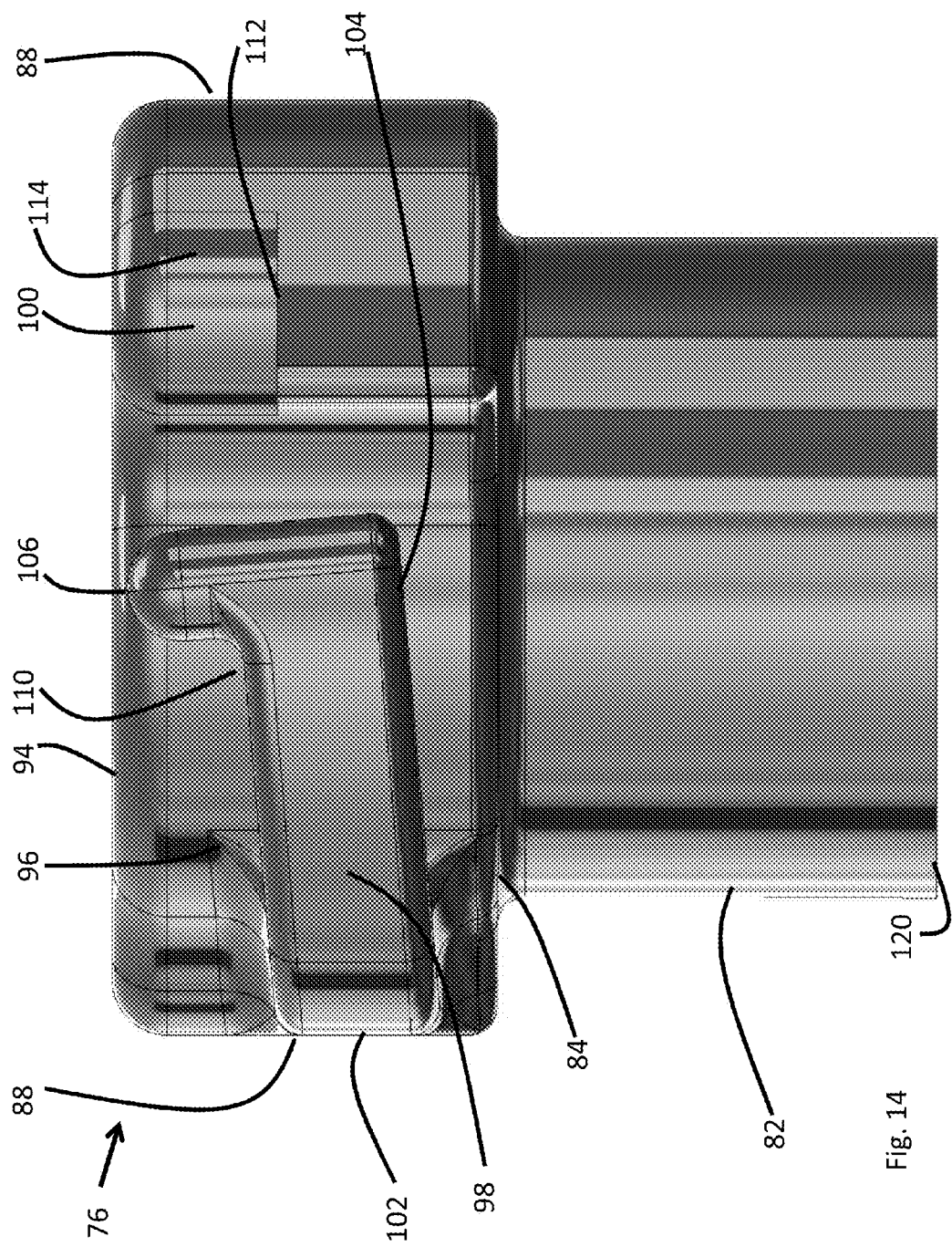
FIG. 14 is a left side view of the locking device of FIGS. 4 and 5.
Figure 15:
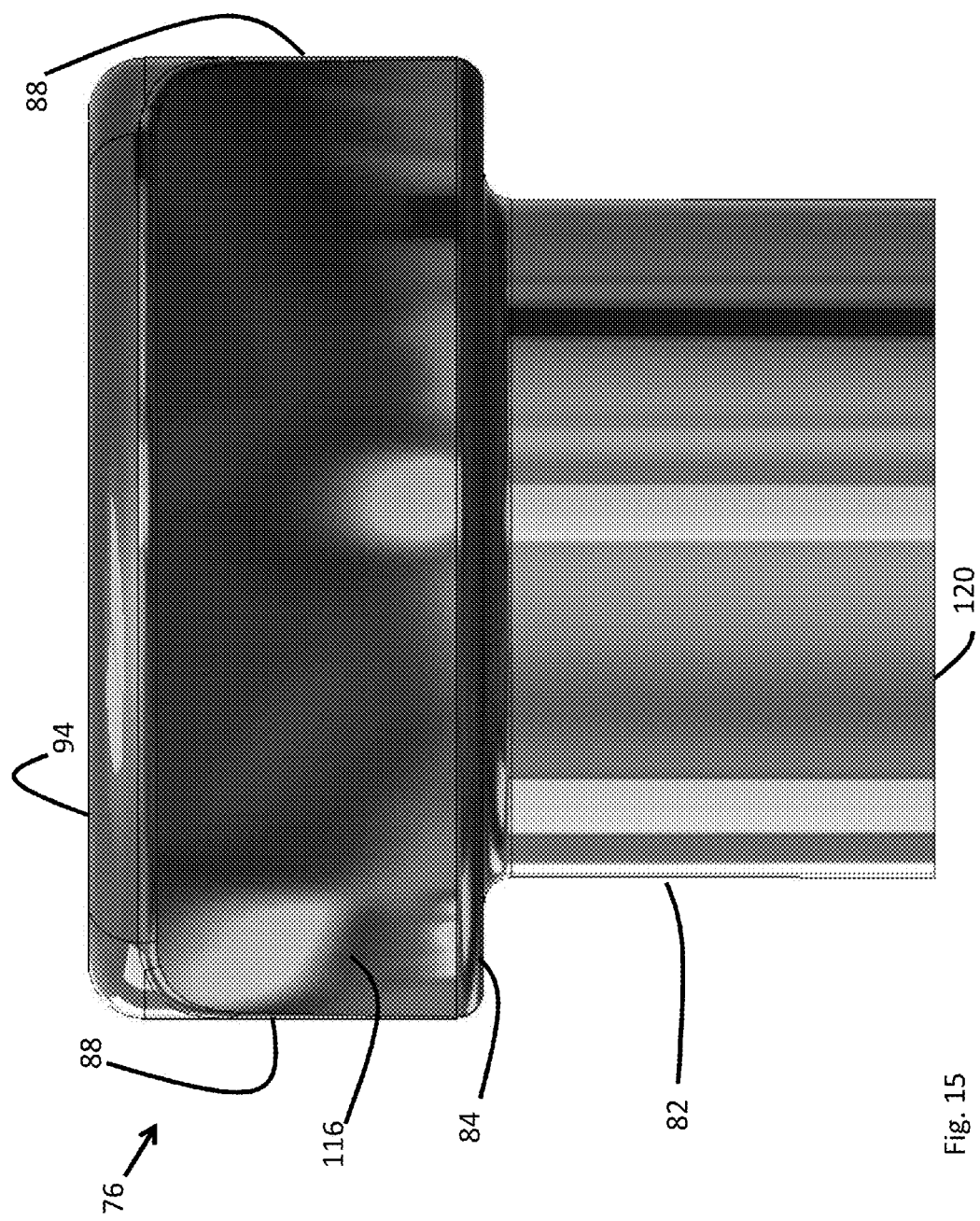
FIG. 15 is a right side view of the locking device of FIGS. 4 and 5.
Figure 16:
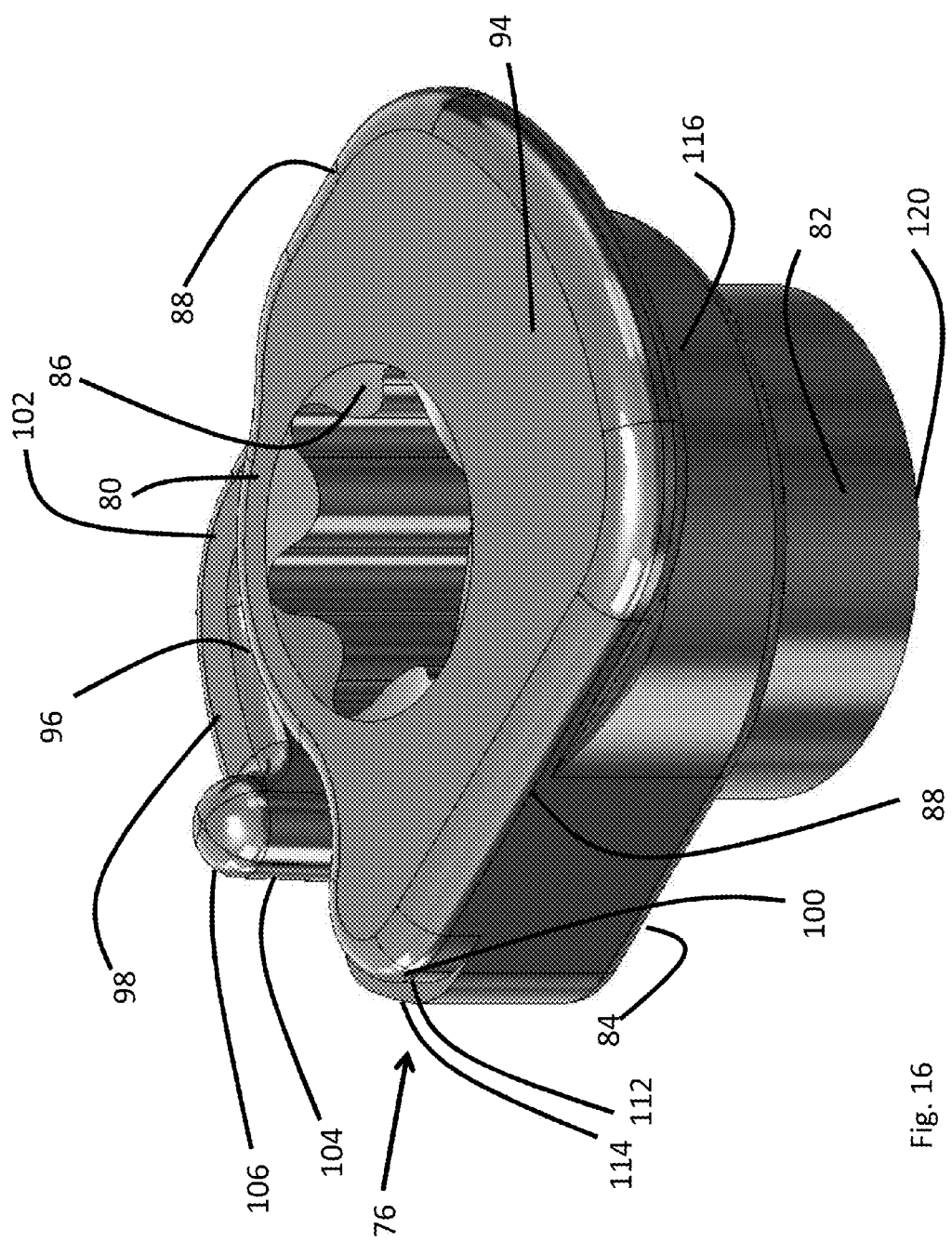
FIG. 16 is a top perspective view of an alternate embodiment of the locking device for a bone fastening mechanism.
Figure 17:
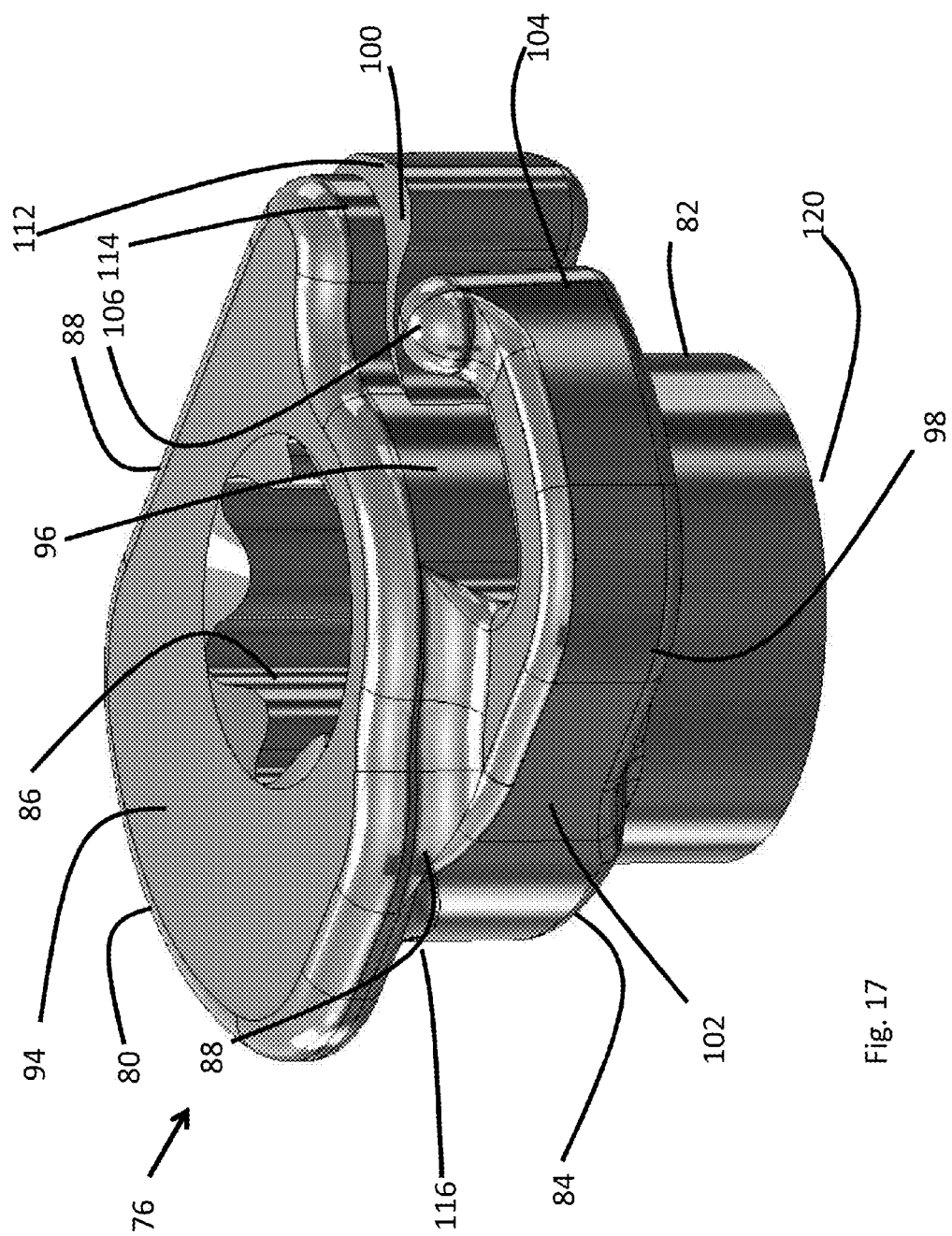
FIG. 17 is an alternate top perspective view of the locking device of FIG. 16.
Figure 18:
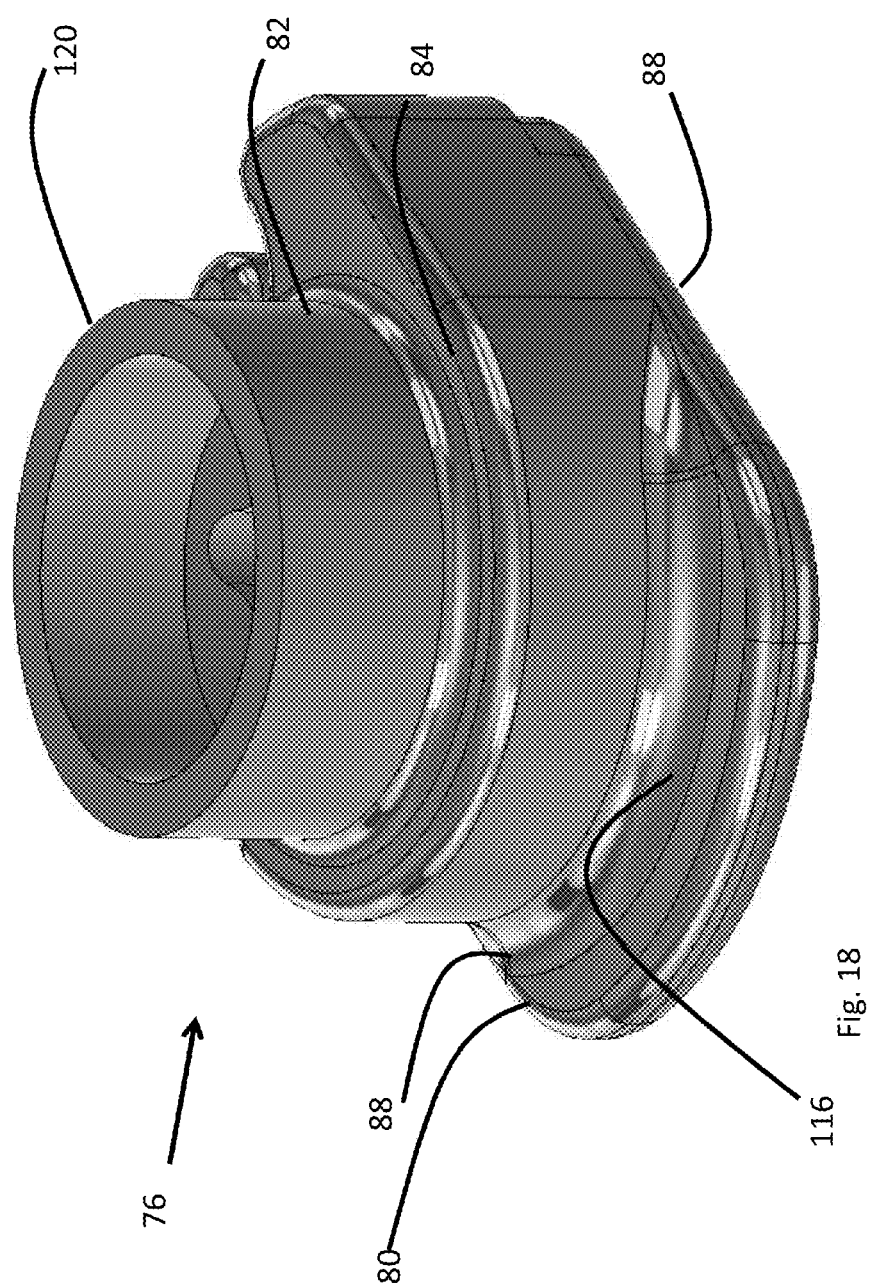
FIG. 18 is a bottom perspective view of the locking device of FIG. 16.
Figure 19:
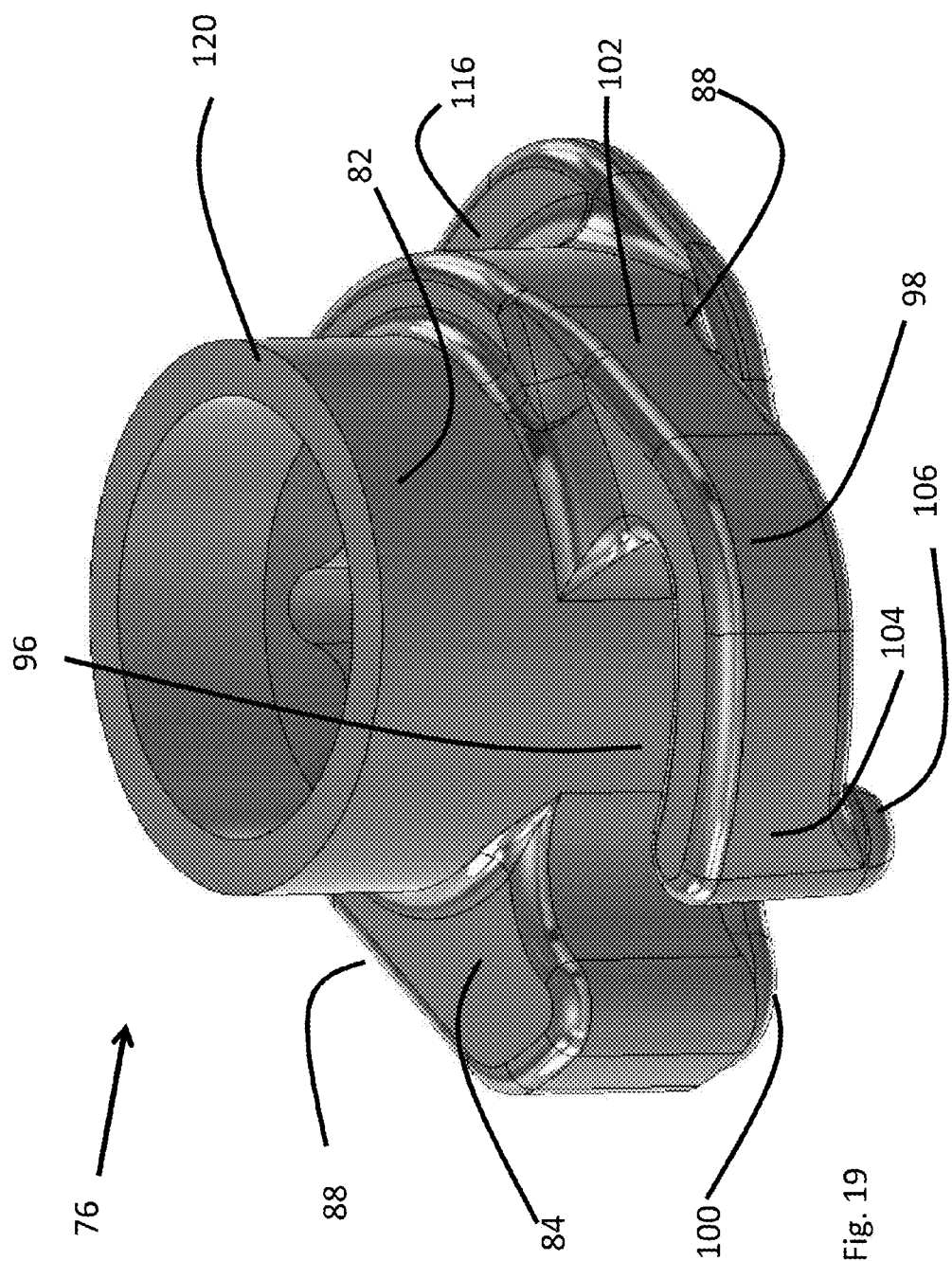
FIG. 19 is an alternate bottom perspective view of the locking device of FIG. 16.
Figure 20:
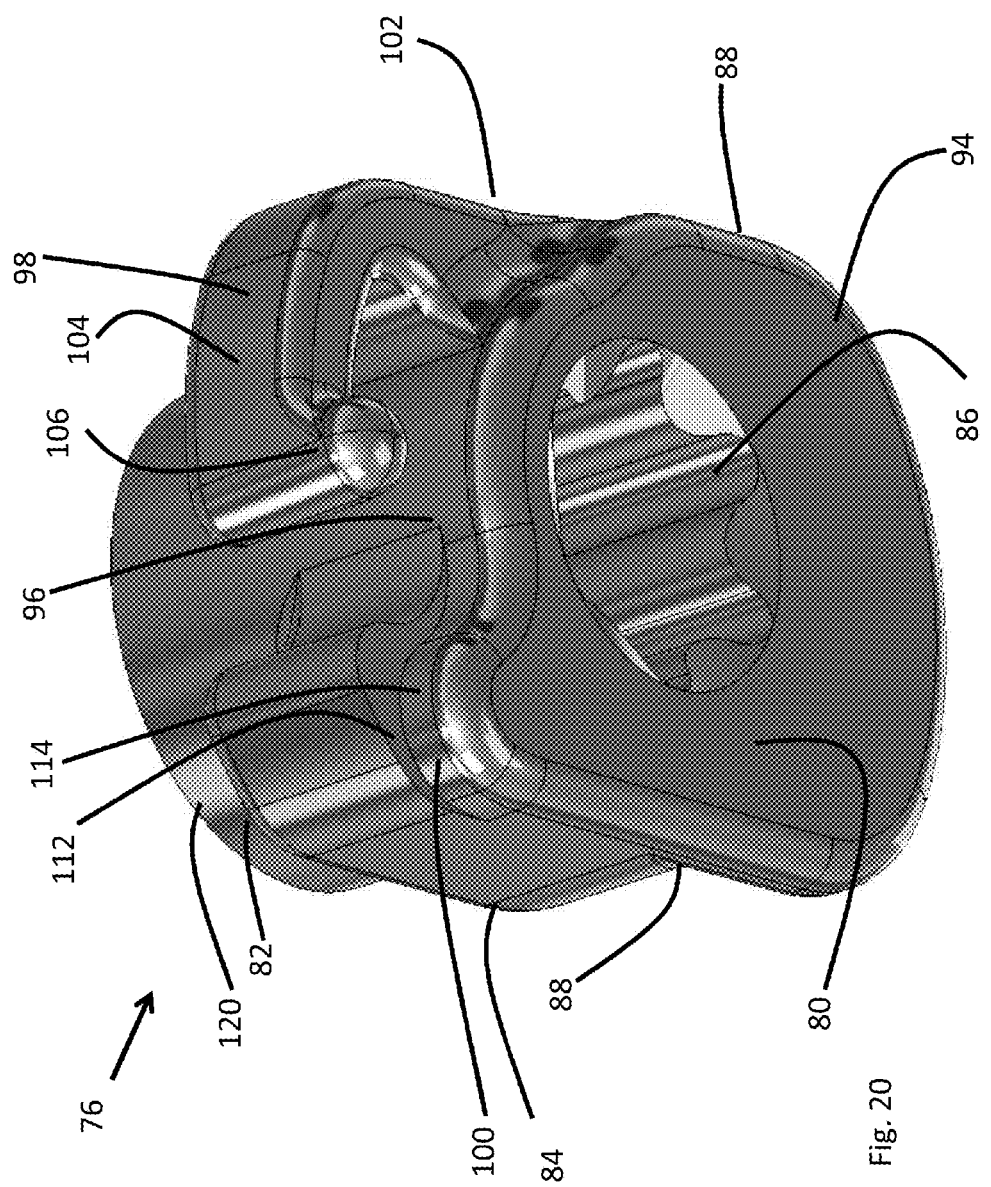
FIG. 20 is an alternate top perspective view of the locking device of FIG. 16.
Figure 21:
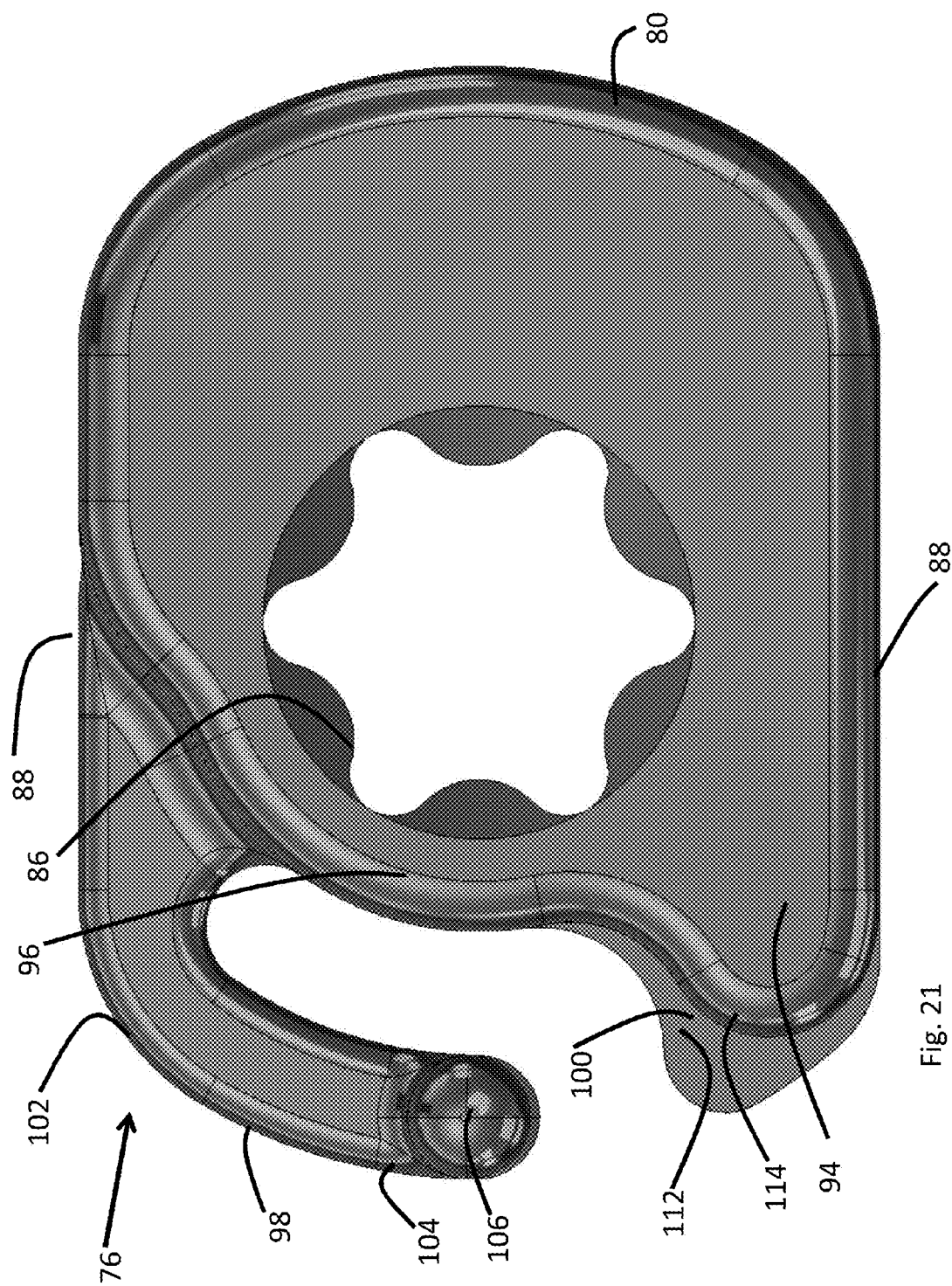
FIG. 21 is a top view of the locking device of FIG. 16.
Figure 22:
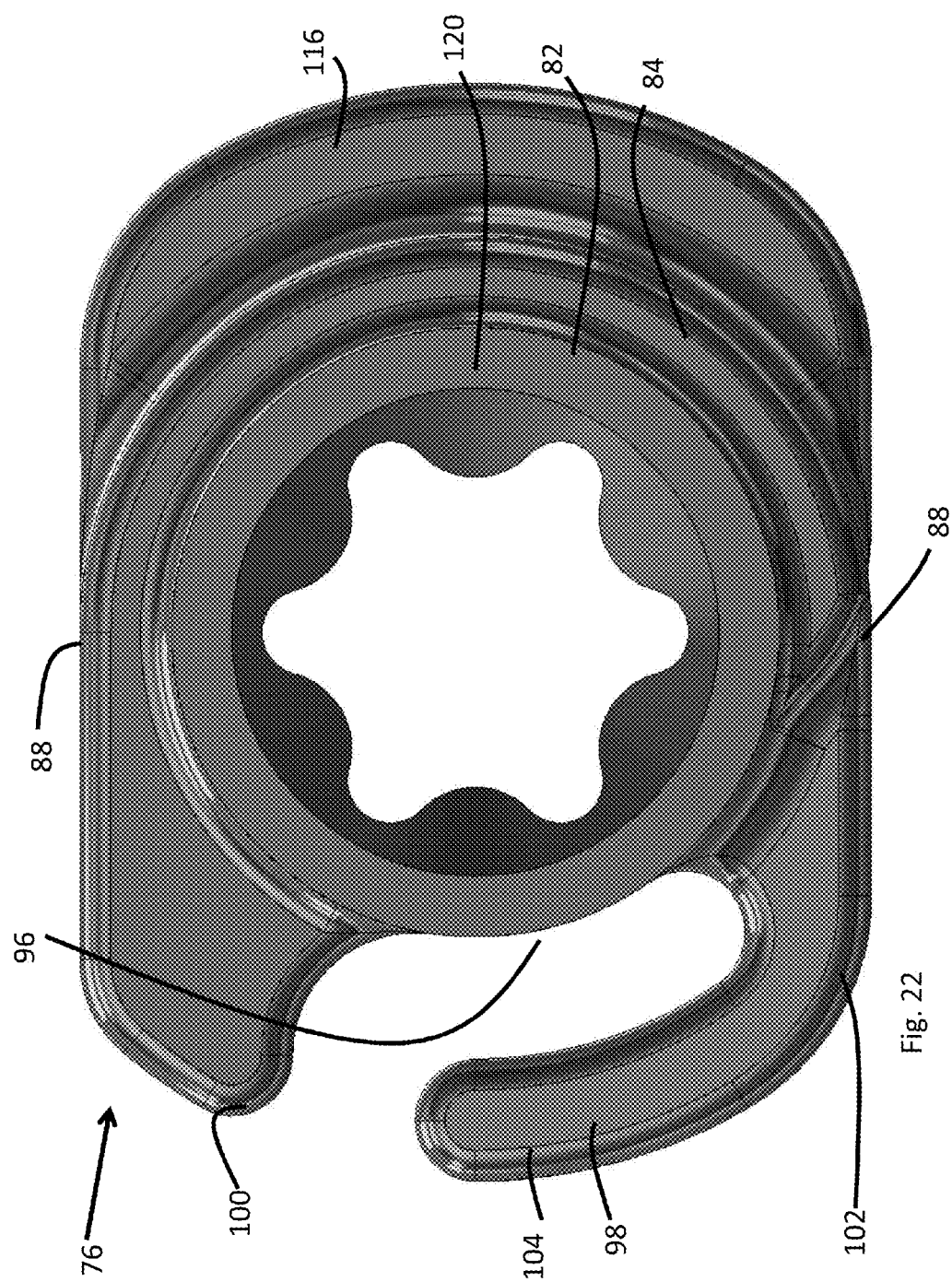
FIG. 22 is a bottom view of the locking device of FIG. 16.
Figure 25:
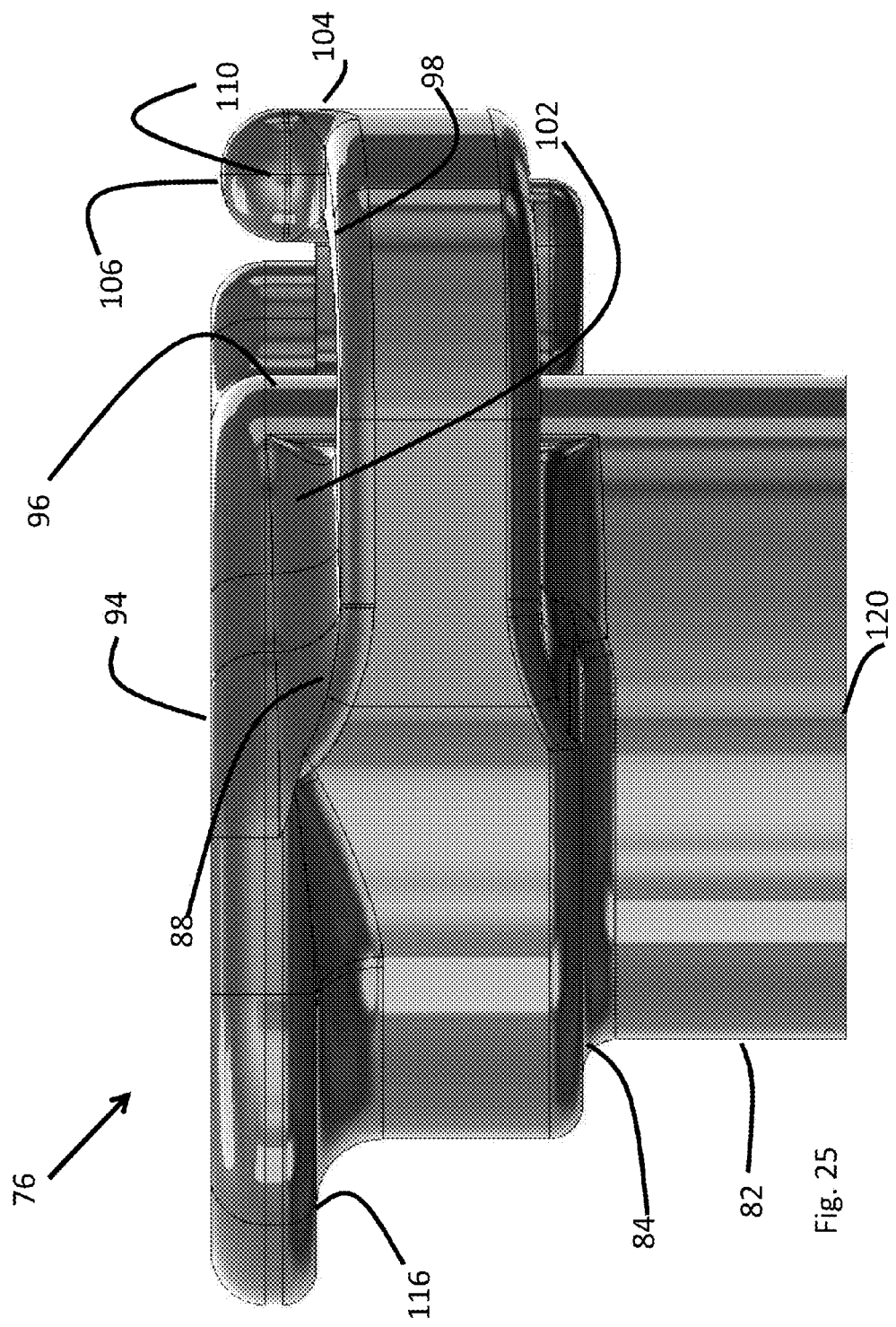
FIG. 25 is a rear view of the locking device of FIG. 16.
Figure 26:
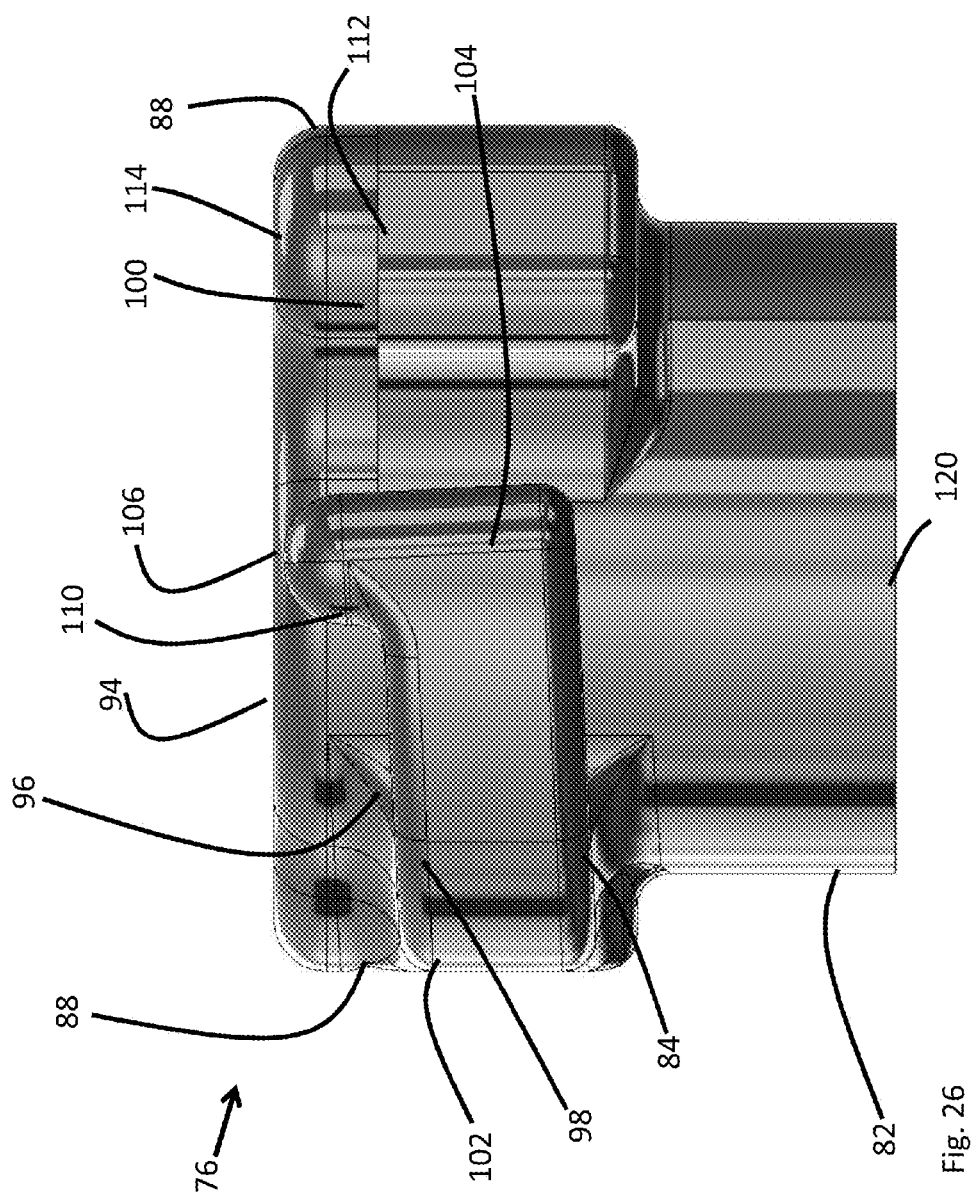
FIG. 26 is a left side view of the locking device of FIG. 16.
Figure 27:
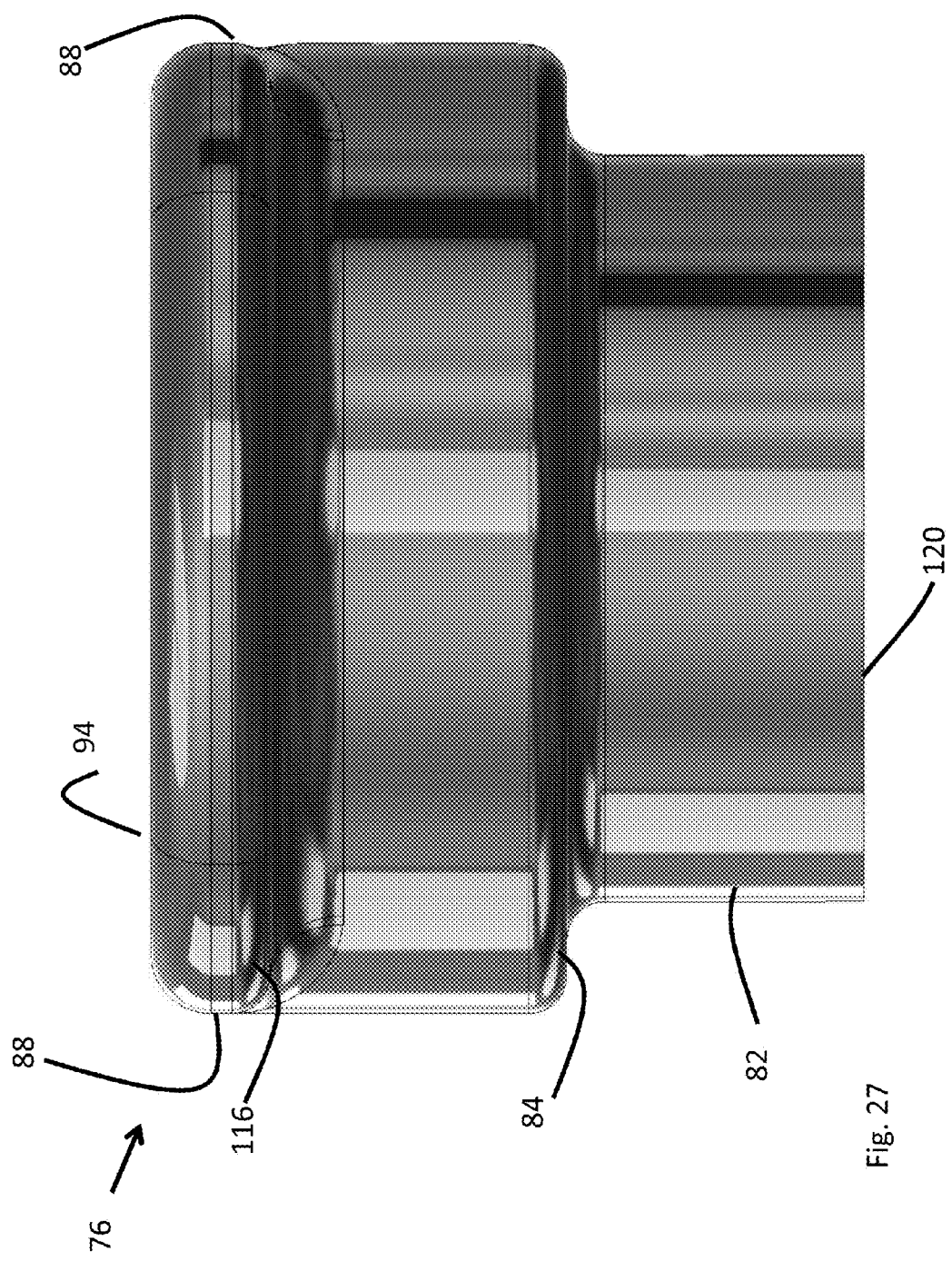
FIG. 27 is a right side view of the locking device of FIG. 16.

As best shown in FIGS. 14 and 26, the arm 98 extends axially upward in the drawing at an angle from a proximal end 102 to a distal end 104 in which a pawl 106 is located. Preferably, the arm angle is about 5 degrees. Thus, the cylindrical surface defining the major diameter 92 is partially relieved or open in the area between the pawl 106 and the positive stop 100 (i.e., counterclockwise from the distal end of the arm where the pawl is located to the positive stop (FIG. 10)). As described previously, the pawl 106 cooperates with the detent 70 formed in the secondary socket to lock the locking device in the second position. As the locking device is rotated from the first or unlocked position (FIG. 4) to the second or locked position (FIG. 5), the angled resilient arm 98 deflects downward as it engages the underside surface of the chord member 68 in the secondary socket. As the arm 98 is deflected downward, the pawl 106 is deflected downward. The distal end 104 of the arm and the pawl 106 include smooth chamfers and fillets 110 (FIGS. 13,25) to enable the pawl to be deflected under the chord member as the locking device is rotated to the second position. FIG. 3 shows the resilient arm 98 being deflected downward by the chord member 68 of the secondary socket in a position intermediate of the unlocked position of FIG. 4 and the locked position of FIG. 5. Once the pawl 106 clears the chord member 68 and enters the detent 70, the resilient arm 98 springs axially outward (i.e., upward in the drawings) to engage the pawl in the detent to lock the locking device in the second position. With the locking device locked in the second position, a portion of the underside 84 of the cap the locking device is positioned in the arcuate cutout 62 to prevent the fixation member 74 from backing out of the primary socket. Accordingly, the resilient arm 98 is preferably not radially deflected as it is rotated from the first to second position to position the pawl 106 in the detent 70. Rather, the arm is axially deflected as the arm engages the underside surface of the chord member of the secondary socket.

To allow further locking of the locking device in the second position, the cap 80 of the locking device is provided with the positive stop 100. The positive stop 100 is arranged on the cap such that the positive stop engages the chord member 68 of the secondary socket when the pawl 106 of the resilient arm is received in the detent 70. The positive stop comprises a flat portion 112 and a wall portion 114 formed in the external relief area 96 adjacent a chord portion 88 of the cap across from the distal end 104 of the arm and pawl 106. As the locking device is rotated from the first to second position (i.e., the position in FIG. 4 to the position in FIG. 5), the positive stop 100 rotates to a position where the flat portion 112 engages the underside of the chord member 68 of the secondary socket and the wall portion 114 engages an upstanding portion of the chord portion. Thus, the positive stop 100 prevents rotation of the locking device while preventing axially outward motion of the locking device in the secondary socket.

The underside surface 84 of the cap portion of the locking device comprises an internal relief area 116 in a portion of an underside surface of the cap. The internal relief area 116 cooperates with the fixation mechanism cap 78 to allow the fixation mechanism to articulate in the primary socket in the receiving member while preventing the fixation member from backing out. In the embodiment shown in FIGS. 6-15, the internal relief area 116 of the cap may have a gentle curvature to cooperate with the geometry associated with an exterior surface of the cap 78 of the fixation mechanism thereby allowing the fixation member to articulate in the receiving member while preventing the fixation member from backing out. In the embodiment shown in FIGS. 16-27, the internal relief area 116 of the cap of the locking device may also be relieved as a more prominent undercut to provide additional clearance for the fixation member cap, depending on the geometry associated with the fixation member cap and the application.

Figure 28:
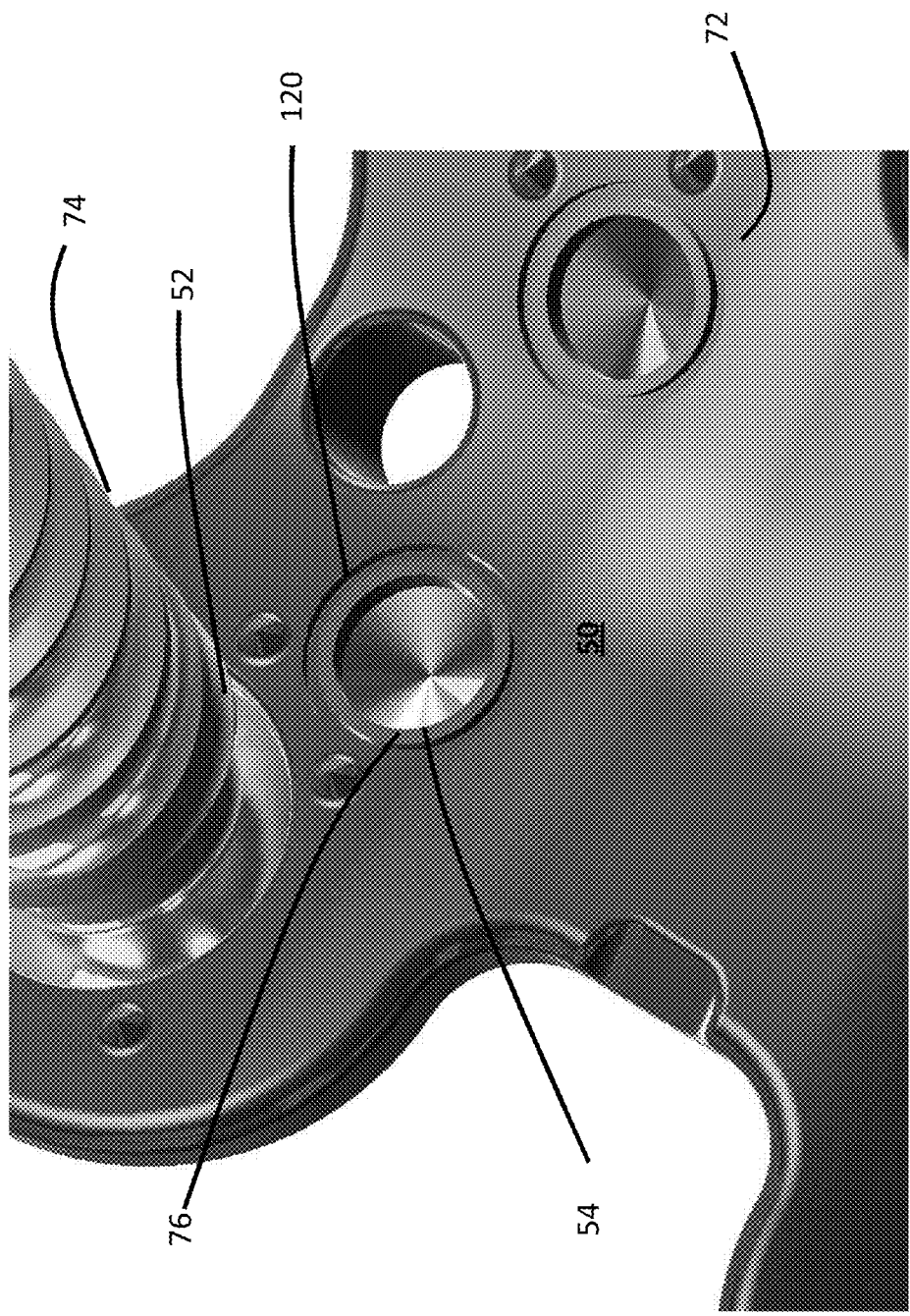
FIG. 28 is a bottom perspective view of the anterior lumbar plate of FIG. 1 showing a locking device installed in the anterior lumber plate.

The locking device may be affixed to the receiving member for rotation of movement within the secondary socket 54 by peening a distal end 120 of the stem 82 of the locking device outward such that the distal end of the stem has a diameter that is larger than the second bore 58 of the secondary socket. FIG. 28 shows further detail of peening over the distal end 120 of the stem such that the diameter associated with the distal end of the stem is larger than the second bore of the secondary socket 54. Other means may also be employed to allow the locking device to be rotatably mounted in the secondary socket. Additionally, as mentioned before, the locking device may be held in the receiving member when the locking device is in the second position by action of the resilient arm engaging the underside of the chord member of the secondary socket, and the positive stop flat which engages the underside of the chord member of the secondary socket.

While specific embodiments have been described in detail and in the foregoing detailed description and illustrated in the accompanied drawings, those with ordinary skill in the art will appreciate that various modifications and alternatives to those details could be developed in light of the overall teachings of the disclosure. Accordingly, the specific embodiments disclosed and particular ranges disclosed were meant to be illustrative only and not limited as to the scope of the invention, which is to be given the full breath of the appended claims and any and all equivalents thereof.

What is claimed is:

1. A receiving member for a bone fixation assembly, the receiving member having opposite first and second sides spaced apart by a thickness, the receiving member comprising a primary socket and a secondary socket on the receiving member first side, the primary socket being adapted to receive a fixation mechanism, the secondary socket being adapted to receive a locking device, the locking device being adapted to engage the fixation mechanism and prevent the fixation member from becoming disengaged from the receiving member primary socket, the primary socket having a bore extending from the primary socket to the receiving member second side thereby allowing a fixation mechanism to be directed into the primary socket and through the bore to a bone anchor site, the secondary socket having first and second bores with the secondary socket first bore being larger in diameter than the secondary socket second bore and forming a shoulder therebetween, the secondary socket first bore intersecting a portion of the primary socket and forming an arcuate cut-out, the secondary socket second bore extending from the secondary socket shoulder into the receiving member thereby enabling a locking device to be directed into the secondary socket and through the secondary socket second bore, the secondary socket having a chord member extending into the secondary socket first bore, the chord member forming a radial undercut between the chord member and the secondary socket shoulder, and the secondary socket having a detent extending from the radial undercut into the chord member.

2. The receiving member of claim 1, wherein the primary socket has a spherical contour.

3. The receiving member of claim 1, wherein the receiving member is an anterior lumbar plate.

4. The receiving member of claim 1, wherein the chord member is generally opposite the arcuate cut-out.

5. The receiving member of claim 1, wherein the secondary socket second bore extends from the shoulder to the receiving member second side.

6. A bone fixation assembly comprising:
   a receiving member having opposite first and second sides spaced apart by a thickness, the receiving member comprising a primary socket and a secondary socket on the receiving member first side, the primary socket having a bore extending from the primary socket to the receiving member second side, the secondary socket having first and second bores with the secondary socket first bore being larger in diameter than the secondary socket second bore and forming a shoulder therebetween, the secondary socket first bore intersecting a portion of the primary socket and forming an arcuate cut-out in the first socket, the secondary socket second bore extending from the secondary socket shoulder into the receiving member, the secondary socket having a chord member extending into the secondary socket first bore, the chord member forming a radial undercut between the chord member and the secondary socket shoulder, and the secondary socket having a detent extending from the radial undercut into the chord member;
   a fixation mechanism adapted to extend through the receiving member primary socket and primary socket bore to a bone anchor site; and
   a locking device having a stem that is configured to be received in the receiving member secondary socket second bore, the locking device having a cap extending from the stem, the cap having an engagement surface and an arm extending from the cap with a pawl extending axially from the arm, the locking device being rotatable in the secondary socket between an unlocked position in which the cap engagement surface is angularly displaced from the arcuate cut-out, and a locked position in which the cap engagement surface occupies the arcute cut-out and engages the fixation mechanism, and the pawl engages the detent with the arm being positioned under the chord member.

7. The bone fixation assembly of claim 6, wherein the chord member deflects the arm as the locking device is rotated to the locked position.

8. The bone fixation assembly of claim 6, wherein the locking device cap engagement surface has a contour that matches a head of the fixation mechanism.

9. The bone fixation assembly of claim 6, wherein the detent is generally centered on the chord portion.

10. The bone fixation assembly of claim 6, where the cap has a protuberance that engages the chord member when the locking device is in the locked position.

11. The bone fixation assembly of claim 6, where in the cap has chord portions defining a minor diameter of the cap.

12. The bone fixation assembly of claim 11, wherein the chord portions provide clearance for the cap in the secondary socket first bore adjacent to the arcuate cut-out when in the locking device is in the unlocked position.

13. The bone fixation assembly of claim 6, wherein the cap has a clearance area to provide clearance for the cap in the secondary socket first bore adjacent to the chord member when the locking device is rotated to the locked position.

14. The bone fixation assembly of claim 6, wherein the secondary socket second bore extends from the shoulder to the receiving member second side.

15. The bone fixation assembly of claim 14, wherein the stem extends through the secondary socket second bore.

16. The bone fixation assembly of claim 15, wherein the stem has a distal end with a diameter larger than the secondary socket second bore.

17. The bone fixation assembly of claim 6, wherein the receiving member primary socket has a spherical contour.

18. The bone fixation assembly of claim 6, wherein the receiving member is an anterior lumbar plate.

19. The bone fixation assembly of claim 6, wherein the secondary socket chord member is generally opposite the arcuate cut-out.

20. The bone fixation assembly of claim 6, wherein the arm extending from the cap is generally diametrically opposite the cap engagement surface.

21. The bone fixation assembly of claim 10, where the protuberance has a flat positioned under the chord member when the locking device is in the locked position.

* * * * *